United States Patent [19]

Itoh et al.

[11] Patent Number: 5,389,663

[45] Date of Patent: Feb. 14, 1995

[54] 1-(1H-1,2,4-TRIAZOLE-YL)-2-PROPANOL COMPOUNDS

[75] Inventors: Katsumi Itoh, Toyono; Kenji Okonogi, Mishima; Akihiro Tasaka, Suita, all of Japan

[73] Assignee: Takeda Chemical Industries, Ltd., Osaka, Japan

[21] Appl. No.: 156,925

[22] Filed: Nov. 24, 1993

Related U.S. Application Data

[63] Continuation of Ser. No. 875,257, Apr. 24, 1992, abandoned.

[30] Foreign Application Priority Data

Apr. 26, 1991 [JP] Japan ................. 3-097638
Jul. 29, 1991 [JP] Japan ................. 3-188871

[51] Int. Cl.[6] ............... A61K 31/595; C07D 249/08
[52] U.S. Cl. ................... 514/383; 514/384;
514/340; 514/381; 514/362; 514/363; 514/365;
514/370; 514/372; 514/236.2; 514/256;
514/275; 514/255; 514/329; 514/310; 548/255;
548/250; 548/251; 548/190; 548/214; 548/127;
548/128; 544/132; 544/298; 544/322; 544/331
[58] Field of Search ............... 548/267.2, 255, 381,
548/190, 214, 127, 128; 514/383, 384, 250, 251,
365, 370, 372, 362, 363, 340, 329, 310, 255, 256,
275, 236.2; 546/276, 210, 141; 544/336, 366,
298, 322, 331, 132

[56] References Cited

FOREIGN PATENT DOCUMENTS

| | | |
|---|---|---|
| 178533 | 4/1986 | European Pat. Off. . |
| 332387 | 9/1989 | European Pat. Off. . |
| 421210 | 4/1991 | European Pat. Off. . |
| 446877 | 9/1991 | European Pat. Off. . |
| 480215 | 4/1992 | European Pat. Off. . |

OTHER PUBLICATIONS

*Chemical and Pharmaceutical Bulletin*, vol. 39, No. 10, Oct. 1991, pp. 2581–2589.

*Primary Examiner*—Mary C. Lee
*Assistant Examiner*—Joseph K. McKane
*Attorney, Agent, or Firm*—Foley & Lardner

[57] ABSTRACT

An azole compound represented by the formula (I):

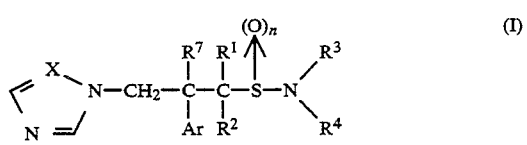

wherein X is a nitrogen atom; Ar is a phenyl group substituted by halogen or a halogenated $C_{1-4}$ alkyl group; $R^1$ and $R^2$ independently are a hydrogen atom or a lower alkyl group, or $R^1$ and $R^2$ may combine together to form a lower alkylene group; n denotes an integer of 0 to 2; and $R^7$ is a hydrogen atom, a hydroxyl group which may be optionally acylated by an acyl group selected from acetyl, propionyl, butyryl, isobutyryl, phenylacetyl and benzoyl, or may form a bond together with $R^1$; or a salt thereof.

8 Claims, No Drawings

1-(1H-1,2,4-TRIAZOLE-YL)-2-PROPANOL COMPOUNDS

This application is a continuation of U.S. application Ser. No. 07/875,257, filed Apr. 24, 1992, now abandoned.

BACKGROUND OF THE INVENTION

1. Field of the invention

The present invention relates to azole compounds useful as antifungal therapeutic agents, their production and use thereof.

2. Prior Art

Various compounds have been known as antifungal agents. For example, as triazole derivatives having antifungal activities, there have been known those having a sulfur-containing group as the side chain bonded to one constituting nitrogen atom of the triazole ring (EP 178,533 and EP 421,210-A2) and those having a nitrogen-containing group as the side chain bonded to one constituting nitrogen atom of the triazole ring (EP 332,387).

Further, other conventional antifungal agents are not satisfactory in their therapeutic effects, because they have various problems such as occurrence of side effects, replacement of fungus and acquisition of drug-resistance.

It would be clear that compounds having higher safety and more potent antifungal activities are desired as therapeutic agents of fungal diseases.

SUMMARY OF THE INVENTION

The present invention is to provide an azole compound represented by the formula (I):

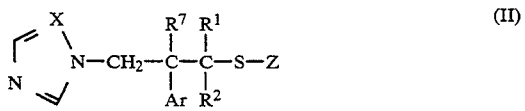
(I)

wherein X is a nitrogen atom or CH; Ar is a substituted phenyl group; $R^1$ and $R^2$ independently are a hydrogen atom or a lower alkyl group, or they may combine together to form a lower alkylene group; B is a group of the formula:

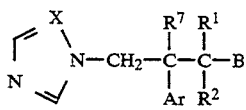

(wherein $R^3$ and $R^4$ independently are a hydrogen atom, an optionally substituted aliphatic or aromatic hydrocarbon residue or an optionally substituted heterocyclic group, or they may form an optionally substituted heterocyclic group together with the nitrogen atom to which they are bonded; and n denotes an integer of 0 to 2), or a group of the formula:

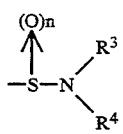

(wherein $R^5$ and $R^6$ independently are a hydrogen atom, an optionally substituted aliphatic or aromatic hydrocarbon residue group or an optionally substituted heterocyclic group, or they may form an optionally substituted heterocyclic group together with the nitrogen atom and sulfur atom to which they are bonded; and m denotes an integer of 0 to 2); and $R^7$ is a hydrogen atom or an optionally acylated hydroxyl group, or may form a bond together with $R^1$, or a salt thereof.

The present invention also provides a process for preparing a compound represented by the above-mentioned formula (I) or its salt, which comprises:

(i) reacting a compound of formula (II):

(II)

wherein Z is an active group and the other symbols have the same meanings as defined in the formula (I), or its salt, thereof, with a compound of formula (III):

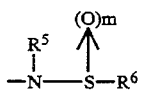
(III)

wherein the symbols have the same meanings as defined in the formula (I), or a salt thereof, and then subjecting the resultant compound to oxidation if necessary, or (ii) reacting a compound represented by the formula (IV):

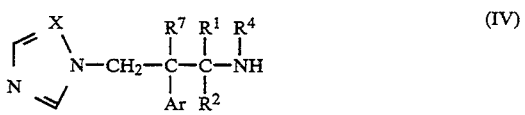
(IV)

wherein the symbols have the same meanings as defined in the formula (I), or a salt thereof, with a compound represented by the formula (V):

(V)

wherein Z' is an active group and the other symbols have the same meanings as defined in the formula (I) or a salt thereof.

Further, the present invention provides an antifungal agent comprising an azole compound represented by the above-mentioned formula (I) or its salt and a carrier or diluent therefor.

The compound of formula (I) or its salt of the present invention is characterized by the substituent B at 3-position of the side chain which is bonded to a nitrogen atom of the azole ring. Specifically, the substituent B has S-N bond or N-S bond as mentioned above.

REFERRED EMBODIMENTS OF THE INVENTION

The substituted phenyl group shown by Ar in the compound of formula (I) is a phenyl group substituted by suitable substituents such as halogen, halogenated $C_{1-4}$ alkyl group or a phenyl group substituted by halogenated $C_{1-4}$ alkyl group in the number of one to four, preferably halogen or halogenated $C_{1-4}$ alkyl group.

More preferably the substituted phenyl group is a phenyl group having 1 to 3 substituents independently selected from a halogen and trifluoromethyl. Preferable examples are 2,4-difluorophenyl, 2,4-dichlorophenyl, 4-fluorophenyl, 4-chlorophenyl, 4-trifluoromethylphenyl, 2-fluoro-4-chlorophenyl, 2-chloro-4-fluorophenyl, 2,4,6-trifluorophenyl and 4-bromophenyl. In particular, 2,4-difluorophenyl or 4-chlorophenyl is preferable as Ar.

The lower alkyl group shown by $R^1$ or $R^2$ in the compound of formula (I) includes straight-chain or branched alkyl groups having one to three carbon atoms such as methyl, ethyl or propyl. Especially, a compound of formula (I) wherein $R^1$ is hydrogen or methyl and $R^2$ is methyl is preferable. Examples of the lower alkylene groups formed by the linkage of $R^1$ with $R^2$ include straight-chain lower (especially $C_{2-4}$) alkylene groups such as ethylene, propylene or butylene, among which ethylene is preferable.

Examples of the optionally substituted aliphatic hydrocarbon residues shown by $R^3$, $R^4$, $R^5$ or $R^6$ include optionally substituted alkyl, cycloalkyl, alkenyl or alkynyl groups.

Examples of the alkyl groups include straight-chain or branched alkyl groups having one to twelve carbon atoms such as methyl, ethyl, propyl, butyl, heptyl, octyl, nonyl, decyl or dodecyl, among which $C_{1-4}$ lower alkyl (e.g., methyl, ethyl, propyl or butyl) is more preferable.

Examples of the cycloalkyl groups include $C_{3-8}$ cycloalkyl groups such as cyclopropyl, cyclobutyl, cyclopentyl, cyclohexyl, cycloheptyl or cyclooctyl, among which $C_{3-6}$ cycloalkyl (e.g., cyclopropyl, cyclobutyl, cyclopentyl or cyclohexyl) is more preferable.

Examples of the alkenyl groups include $C_{2-4}$ alkenyl groups such as vinyl, propenyl or butenyl, among which $C_{2-3}$ alkenyl group (e.g., vinyl or propenyl) is more preferable.

Examples of the alkynyl groups include $C_{2-4}$ alkynyl, such as 4,4-dimethyl-2-pentynyl or 6,6-dimethyl-2-hepten-4-ynyl, preferably $C_{2-4}$ alkynyl groups such as ethynyl, propynyl or butynyl, among which $C_{2-3}$ alkynyl group (e.g., ethynyl or propynyl) is more preferable.

Examples of the optionally substituted aromatic hydrocarbon residues shown by $R^3$, $R^4$, $R^5$ or $R^6$ include optionally substituted aryl groups having six to fourteen carbon atoms such as phenyl, naphthyl, biphenyl, anthryl or indenyl. In particular, aryl group having six to ten carbon atoms (e.g., phenyl or naphthyl) is preferable.

Examples of the heterocyclic groups in the optionally substituted heterocyclic groups shown by $R^3$, $R^4$, $R^5$ or $R^6$ include 5-or 6-membered heterocyclic groups containing at least one hetero atom selected from a nitrogen atom, sulfur atom and oxygen atom, such as imidazolyl, triazolyl, tetrazolyl, pyrazolyl, pyridyl, thiazolyl, thiadiazolyl, thienyl, furyl, pyrrolyl, pyrazinyl, 4-piperidinyl, 1-piperazinyl, pyrimidinyl, isoxazolyl, oxazolyl, N-methylimidazolyl or N-methyltriazolyl. Preferable heterocyclic groups are 5- or 6-membered aromatic heterocyclic groups containing one to three hetero atoms optionally selected from a nitrogen atom, sulfur atom and oxygen atom, for example, imidazolyl, triazolyl, thiazolyl, thiadiazolyl, thienyl, furyl, pyridyl or pyrimidinyl.

When $R^3$ and $R^4$ form an optionally substituted heterocyclic ring together with the nitrogen atom to which they are bonded, the heterocyclic group may further contain at least one hetero atom selected from a nitrogen atom, sulfur atom and oxygen atom. The group is preferably exemplified by morpholino, piperidino, 1-piperazinyl, 1-pyrrolidinyl, 1,2,2,4-tetrahydropyrazin-1-yl, 1-indolinyl, 2-isoindolinyl, 1,2,3,4-tetrahydroquinolin-1-yl, 1,2,3,4tetrahydroisoquinolin-2-yl, inidazolyl, triazolyl, tetrazolyl, pyrrolyl, pyrazolyl or the like. In particular, non-aromatic 5- or 6-membered heterocyclic group (e.g., morpholino, 1-pyrrolidinyl or 1-piperazinyl) is preferable.

When an optionally substituted heterocyclic ring is similarly formed by $R^5$ and $R^6$ together with the nitrogen atom and sulfur atom to which they are bonded, the heterocyclic group is preferably exemplified by 2-isothiazolidinyl, dihydro-2-isothiazolyl, perhydro-1, 2-thiazin-2-yl or the like, among which 2-isothiazolidinyl is especially preferable.

The substituent(s) of the substituted aliphatic or aromatic hydrocarbon residue and substituted heterocyclic group shown by $R^3$, $R^4$, $R^5$ and $R^6$ in the compound of formula (I) are exemplified by a hydroxyl group, optionally esterified carboxyl group (e.g., carboxyl, methoxycarbonyl, ethoxycarbonyl or butoxycarbonyl), nitro group, amino group, acylamino group (e.g., $C_{1-6}$ alkanoylamino group such as acetylamino, propionylamino or butyrylamino), $C_{1-6}$ alkylamino group (e.g., methylamino, dimethylamino, diethylamino or dibutylamino), $C_{1-6}$ alkoxy group(e.g., methoxy, ethoxy or butoxy), halogen (e.g., fluorine, chlorine or bromine), halogenated $C_{1-3}$ alkyl group (e.g., trifluoromethyl, dichloromethyl or trifluoroethyl), oxo group, thiox group, mercapto group, $C_{1-6}$ alkylthio group (e.g., methylthio, ethylthio or butylthio), $C_{1-6}$ alkylsulfonyl group (e.g., methanesulfonyl, ethanesulfonyl or butanesulfonyl), $C_{1-6}$ alkanoyl group (e.g., acetyl, formyl, propionyl or butyryl), $C_{6-14}$ aryl group optionally substituted with ① optionally halogenated $C_{1-3}$ alkyl group, ② halogen, ③ optionally halogenated $C_{1-3}$ alkoxy group, ④ heterocyclic group (heterocyclic group is as mentioned above) which may optionally be substituted with (i) optionally halogenated $C_{1-6}$ alkyl group, (ii) $C_{1-6}$ alkylsulfonyl group or (iii) $C_{1-6}$ alkylthio group (e.g., phenyl, naphthyl, tolyl, fluorophenyl, bromophenyl, methoxyphenyl, trifluoroethoxyphenyl, trifluoromethylphenyl, 4-(1H-1,2,4-triazol-1-yl )phenyl, 4-(4H-1,2,4-triazol-4-yl)phenyl, 4-[2-(2-butyl)-3,4-dihydro-3-oxo-2H-1,2,4-triazol-4-yl]phenyl or 4-[3,4-dihydro-2-(2,2,2-trifluoroethyl)-3-oxo-2H-1,2,4-triazol-4-yl]phenyl), benzoyl group optionally substituted by halogen or halogenated $C_{1-3}$ alkyl group (e.g., benzoyl, fluorobenzoyl, trifluoro-methylbenzoyl or difluorobenzoyl), heterocyclic alkyl group (e.g., triazolylmethyl, methyltriazolylmethyl, pyridylmenthyl, imidazolylmethyl or methylimidazolylmethyl) and $C_{3-6}$ cycloalkyl-alkyl group (e.g., cyclopropylmethyl or cyclopentylmethyl). The substituent also includes the optionally substituted alkyl group, optionally substituted cycloalkyl group, optionally substituted alkynyl group and optionally substituted heterocyclic group as defined for $R^3$, $R^4$, $R^5$ and $R^6$ In particular a halogen halogenated alkyl group, optionally substituted aryl group or optionally substituted heterocyclic group is preferable.

Further, when $R^3$ and $R^4$ form a heterocyclic ring together with the nitrogen atom to which they are bonded, the heterocyclic group may optionally have such substituents as described above. The preferable examples of substituents are esterified carboxyl, $C_{6-14}$ aryl group optionally substituted with ① optionally halogenated $C_{1-3}$ alkyl group, ②  halogen, ③ optionally halogenated $C_{1-3}$ alkoxy group or ④ heterocyclic group which may optionally be substituted with $C_{1-4}$ alkyl group.

When $R^5$ and $R^6$ form a heterocyclic ring together with the nitrogen atom and sulfur atom to which they are bonded, the heterocyclic ring may optionally have such substituents as described above.

When the groups represented by $R^3$, $R^4$, $R^5$ and $R^6$ are substituted alkyl group, preferable examples thereof include fluorine-substituted ($C_{1-4}$) alkyl groups (e.g., trifluoroethyl, 2,2,2-trifluoroethyl or 3-chloropropyl) and optionally substituted heterocycle-($C_{1-4}$) alkyl groups (e.g., 4-methyl-4H-1,2,4-triazol-3-ylmethyl, 1-methyl- 2-imidazolylmethyl, 2-thiazolylmethyl, 4-methyl-5-thiazolylethyl, 5-methylthio-1,3,4-thiadiazole-2-ylmethyl, 5-methylthio- 1,3,4-thiadiazole-2-ylethyl, 5-methyl sulfonyl-1,3,4-thiadiazole-2-ylethyl, 2-pyridylmethyl, 3-pyridylmethyl or 4-pyridylmethyl).

Examples of the acyl groups in the optionally acylated hydroxyl group shown by $R^7$ include acyl groups derived from aliphatic or aromatic monocarboxylic acid, such as acetyl, propionyl, butyryl, isobutyryl, phenylacetyl and benzoyl. Preferable ones are those which are hydrolyzable in vivo.

When $R^7$ and $R^1$ of the compound of formula (I) together form a bond, the same compound can be shown by the formula (I').

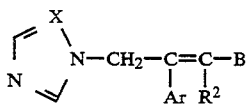
(I')

wherein the symbols have the same meanings as defined above.

A preferred groups of the compounds of formula (I) of this invention is represented by the formula (Ia):

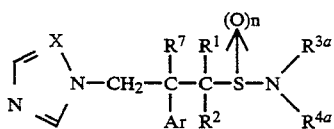
(Ia)

wherein X is a nitrogen atom; Ar is a substituted phenyl group; $R^1$, $R^2$, $R^7$ and n have the same meanings as defined in the formula (I); and $R^{3a}$ and $R^{4a}$ are, the same or different, an optionally substituted aliphatic or aromatic hydrocarbon residue or an optionally substituted heterocyclic group, or they may form a heterocyclic group together with the nitrogen atom to which they are bonded.

The optionally substituted aliphatic or aromatic hydrocarbon rediues or the optionally substituted heterocyclic groups represented by $R^{3a}$ or $R^{4a}$ are the same as those defined for $R^3$ or $R^4$. Another preferred group of the compound of formula (I) is represented by the formula (Ib):

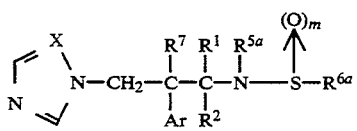
(Ib)

wherein X is a nitrogen atom; Ar is a substituted phenyl group; $R^1$, $R^2$, $R^7$ and m have the same meanings as defined in the formula (I); and $R^{5a}$ and $R^{6a}$ are, the same or different, a hydrogen atom, an optionally substituted aliphatic or aromatic hydrocarbon residue or an optionally substituted heterocyclic group, or they may form a heterocyclic group together with the nitrogen atom and sulfur atom to which they are bonded.

The optionally substituted aliphatic or aromatic hydrocarbon rediues or the optionally substituted heterocyclic groups represented by $R^{5a}$ or $R^{5a}$ are the same as those defined for $R^5$ or $R^6$.

Still another preferred group of the compounds of formula (I) is represented by the formula (Ic):

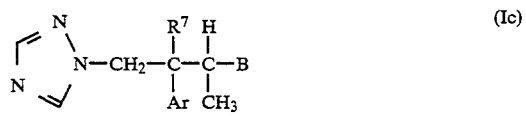
(Ic)

wherein Ar is a halogen-substituted phenyl group; and $R^7$ and B have the same meanings as defined in the formula (I), Further, preferable compounds of formula (I) are those wherein X, Ar, $R^1$, $^2 R^7$ have the same meanings as defined above; and B is a group of the formula:

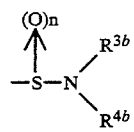

wherein $R^{3b}$ and $R^{4b}$ are, independently, a hydrogen atom or an optionally substituted alkyl group having one to twelve carbon atoms, and n has the same meaning as defined above, or a group of the formula:

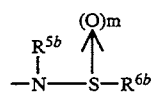

wherein $R^{5b}$ and $R^{6b}$ are independently a hydrogen atom or an optionally substituted $C_{1-12}$ alkyl group, and m has the same meaning as defined above.

Other preferable compounds of formula (I) are those wherein n or m is an integer of 2 and the other symbols have the same meanings as defined above.

In the compound of formula (Ic), it is preferable that the carbon atom to which the substituted phenyl group represented by Ar is bonded and the carbon atom to which $R^2$ is bonded are R-configurated.

Specific examples of preferable ones belonging to the compound of formula (I) of this invention are shown in Tables 1, 2 and 3.

TABLE 1

Structure:
2,4-difluorophenyl group with (R),(R) stereochemistry; 1,2,4-triazol-1-ylmethyl, hydroxyl, and CH(CH₃)-S(O)$_n$-NR³R⁴ substituents at the central carbon.

| Compound No. | n | $-N\begin{smallmatrix}R^3\\R^4\end{smallmatrix}$ |
|---|---|---|
| 1 | 0 | $-N(CH_3)_2$ |
| 2 | 2 | $-N(CH_3)_2$ |
| 3 | 0 | $-NH(CH_2)_3CH_3$ |
| 4 | 2 | $-NH(CH_2)_3CH_3$ |
| 5 | 0 | $-NH$-cyclohexyl |
| 6 | 2 | $-NH$-cyclohexyl |
| 7 | 0 | morpholino ($-N(CH_2CH_2)_2O$) |
| 8 | 2 | morpholino ($-N(CH_2CH_2)_2O$) |
| 9 | 0 | $-NH$-cyclopropyl |
| 10 | 2 | $-NH$-cyclopropyl |
| 11 | 0 | $-NH-CH_3$ |
| 12 | 2 | $-NH-CH_3$ |
| 13 | 0 | $-NH-CH_2CH_3$ |
| 14 | 2 | $-NH-CH_2CH_3$ |
| 15 | 0 | $-NH-(CH_2)_2CH_3$ |
| 16 | 2 | $-NH-(CH_2)_2CH_3$ |
| 17 | 0 | 4-(tert-butoxycarbonyl)piperazin-1-yl |
| 18 | 1 | 4-(tert-butoxycarbonyl)piperazin-1-yl |
| 19 | 2 | 4-(tert-butoxycarbonyl)piperazin-1-yl |
| 20 | 2 | piperazin-1-yl ($-N(CH_2CH_2)_2NH$) |
| 21 | 0 | $-NH$-(4-bromophenyl) |
| 22 | 2 | $-NH$-(4-bromophenyl) |
| 23 | 2 | 4-phenylpiperazin-1-yl |
| 24 | 2 | 4-(4-trifluoromethylbenzoyl)piperazin-1-yl |
| 25 | 2 | 4-acetylpiperazin-1-yl |
| 26 | 2 | 4-[(1-methyl-1H-1,2,4-triazol-5-yl)methyl]piperazin-1-yl |
| 27 | 0 | pyrrolidin-1-yl |

TABLE 1-continued

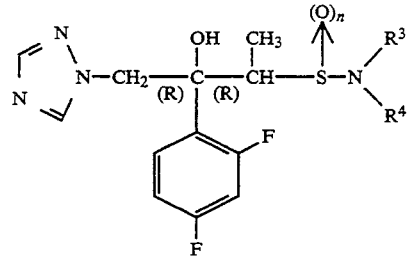

| Compound No. | n | −N(R³)(R⁴) |
|---|---|---|
| 28 | 2 | pyrrolidin-1-yl |
| 38 | 0 | −NHCH$_2$CF$_3$ |
| 39 | 2 | −NHCH$_2$CF$_3$ |
| 40 | 0 | −NHCH$_2$-(1-methyl-1,2,4-triazol-5-yl) |
| 41 | 2 | −NHCH$_2$-(1-methyl-1,2,4-triazol-5-yl) |
| 42 | 2 | 4-(4-methylpiperazin-1-yl)phenyl-triazolone with N-CH(CH$_3$)CH$_2$CH$_3$ |
| 43 | 2 | 4-(4-methylpiperazin-1-yl)phenyl-triazolone with N-CH(CH$_3$)CH$_2$CH$_3$ |
| 44 | 2 | 4-(4-methylpiperazin-1-yl)phenyl-triazolone with NCH$_2$CF$_3$ |
| 45 | 2 | 4-(pyrimidin-2-yl)piperazin-1-yl |
| 46 | 2 | −N(CH$_3$)CH$_2$CF$_3$ |

TABLE 1-continued

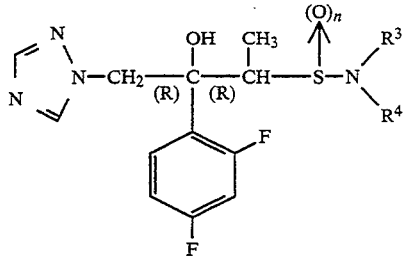

| Compound No. | n | −N(R³)(R⁴) |
|---|---|---|
| 47 | 2 | −N(CH$_3$)CH$_2$C$_6$H$_5$ |
| 48 | 2 | −N(CH$_3$)CH$_2$CH$_3$ |
| 58 | 2 | −NHCH$_2$C$_6$H$_5$ |
| 59 | 2 | −NHCH(C$_6$H$_5$)$_2$ |
| 60 | 2 | −NHCH$_2$-(3,4-dimethoxyphenyl) |
| 61 | 2 | −N(CH$_3$)C$_{12}$H$_{25}$ |
| 62 | 2 | −N(CH$_3$)CH$_2$C≡CH |
| 63 | 2 | −N(CH$_3$)CH$_2$C≡C−C(CH$_3$)$_3$ |
| 64 | 2 | −N(CH$_3$)CH$_2$-(pyridin-3-yl) |

TABLE 1-continued

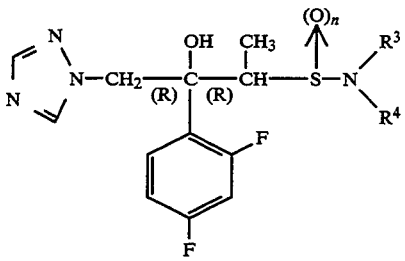

| Compound No. | n | —N(R³)(R⁴) |
|---|---|---|
| 65 | 2 | —NH₂ |
| 66 | 2 | —N(CH₃)CH₂—C₆H₄—4-CF₃ |
| 67 | 2 | —N(CH₃)CH₂—C₆H₃(2-F)(4-CF₃) |
| 68 | 2 | —N(CH₃)CH₂—CH=CH—C≡C—C(CH₃)₃ (E) |
| 69 | 2 | —N(CH₃)CH₂—CH=CH—C≡C—C(CH₃)₃ (Z) |
| 70 | 2 | —N(piperazinyl)—C₆H₄—4-OCH₂CF₃ |
| 71 | 2 | —N(piperazinyl)—C₆H₄—4-F |
| 72 | 2 | —N(piperazinyl)—C₆H₄—4-OCH₃ |
| 73 | 2 | —N(piperazinyl)—C₆H₄—4-CF₃ |
| 74 | 2 | —N(piperazinyl)-2-pyridyl |
| 75 | 2 | —N(CH₃)CH₂-(1-methylimidazol-2-yl) |
| 76 | 2 | —N(CH₃)CH₂-4-pyridyl |
| 77 | 2 | —N(CH₃)-2-pyrimidinyl |
| 78 | 2 | —N(CH₃)CH₂-2-thiazolyl |
| 79 | 2 | —N(CH₃)CH₂-2-pyridyl |
| 80 | 2 | —N(CH₃)CH₂CH₂—C(CH₃)=C(thiazolyl) |
| 81 | 2 | —N(CH₃)—C(=N—N=C(CH₃))—S— |
| 82 | 2 | —N(CH₃)CH₂—C(S)=N—N=C(SCH₃) |

TABLE 1-continued
[Structure showing triazole-CH2-C(OH)(2,4-difluorophenyl)-CH(CH3)-S(O)n-NR3R4 with (R),(R) stereochemistry for compound 29]
| Compound No. | n | -N(R3)(R4) |
|---|---|---|
| 83 | 2 | [-N(CH3)-CH2CH2-thiadiazole-SCH3] |
| 84 | 2 | [-N(CH3)-CH2CH2-thiadiazole-SO2CH3] |
| 91 | 2 | [piperazinyl-pyrimidine with Cl and F substituents] |
| 92 | 2 | [piperazinyl-fluoropyrazine] |
TABLE 2
| Compound No. | Structure |
|---|---|
| 29 | 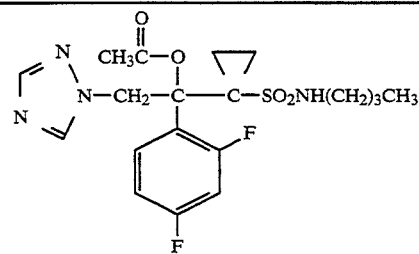 |
| 30 (isomer A) / 31 (isomer B) | 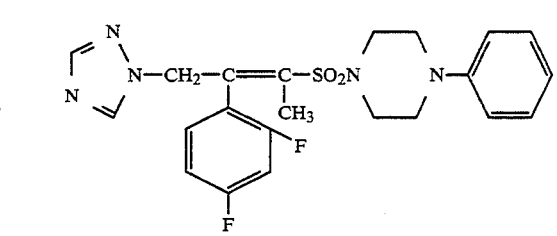 |
| 32 (isomer A) / 33 (isomer B) | 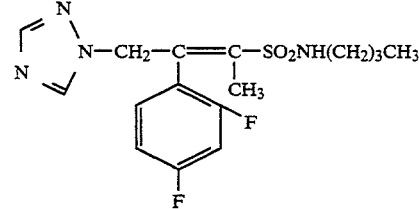 |
| 34 (isomer A) / 35 (isomer B) | 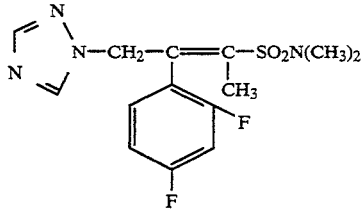 |

TABLE 2-continued

| Compound No. | Structure |
|---|---|
| 36 (isomer A) 37 (isomer B) | triazole-N-CH₂-C(=C(CH₃)-SO₂NH₂)-(2,4-difluorophenyl) |
| 85 | imidazole-N-CH₂-C(R)(OH)(2,4-difluorophenyl)-CH(R)(CH₃)-SO₂N(CH₃)₂ |
| 86 | imidazole-N-CH₂-C(R)(OH)(2,4-difluorophenyl)-CH(R)(CH₃)-SO₂N(CH₃)(CH₂-C₆H₄-4-CF₃) |

TABLE 3 triazole-N-CH₂-C(R)(OH)(2,4-difluorophenyl)-CH(R)(CH₃)-B

| Compound No. | —B |
|---|---|
| 49 | —NHSO₂CH₃ |
| 50 | —NHSO₂-(2,4-difluorophenyl) |
| 51 | —NHSO₂-(4-nitrophenyl) |
| 52 | —NHSO₂-(4-aminophenyl) |
| 53 | —N(CH₃)(SO₂CH₃) |

TABLE 3-continued triazole-N-CH₂-C(R)(OH)(2,4-difluorophenyl)-CH(R)(CH₃)-B

| Compound No. | —B |
|---|---|
| 54 | —N(CH₃)(SO₂CH₂CF₃) |
| 55 | —NHSO₂CH₂CF₃ |
| 56 | —NHSO₂(CH₂)₃Cl |
| 57 | cyclic —N-SO₂-(CH₂)₃- |
| 87 | —NHSO₂-(2-thienyl) |

TABLE 3-continued

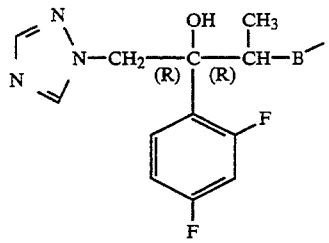

| Compound No. | —B′ |
|---|---|
| 88 | 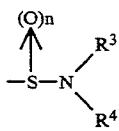 (structure with —N(CH₃)SO₂— linked to N-methylimidazole) |
| 89 | (structure with —N(CH₃)SO₂— linked to thiazole bearing CH₃, H₃C, and NHC(O)CH₃) |
| 90 | (structure with —N(CH₃)SO₂— linked to thiophene) |
| 93 | (structure with —N(SO₂CH₃)CH₂— linked to pyridine) |
| 94 | (structure with —N(SO₂CH₃)CH₂— linked to pyridine) |
| 95 | (structure with —N(SO₂CH₃)CH₂— linked to 4-CF₃-phenyl) |

A compound of formula (I), wherein B is a group of the formula:

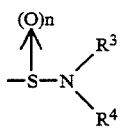

and n is 0, or its salt, can be produced by, for example, reacting a compound of formula (II):

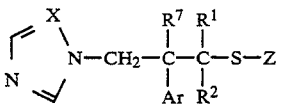

wherein Z is an active group and the other symbols have the same meanings as defined above, or its salt, with a compound of formula (III):

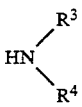

wherein the symbols have the same meanings as defined above, or its salt.

The group represented by Z in the compound of formula (II) is an active group which can be removed by the reaction with the amine (III). Although a halogen atom such as a chlorine atom is preferable for Z, specific limitation should not be made for Z.

The reaction can be allowed to proceed, usually, in an organic solvent such as halogenated hydrocarbons (e.g., dichloromethane or chloroform), alcohols (e.g., methanol, ethanol, propanol, isopropanol or butanol), ethers (e.g., tetrahydrofuran, dioxane or diethylether), amides (e.g., N,N-dimethylformamide or dimethylacetamide), ketones (e.g., acetone or methylethylketone), esters (e.g., ethyl acetate, methyl acetate), hydrocarbons (e.g., benzene, toluene, hexane, xylene or petroleum benzine), nitriles (e.g., acetonitrile) singly or in a mixture thereof, while keeping the reaction system at a temperature ranging from about $-20°$ C. to about $+100°$ C. The reaction time is about 30 minutes to 24 hours. The amount of the organic solvent to be used is about 5 to 100 equivalents to 1 mol of the compound (II) or (III). In this case, for accelerating the reaction rate, a base such as triethylamine, pyridine, 4-dimethylaminopyridine or picoline can be allowed to coexist in the reaction system.

A compound of formula (I), wherein B is a group of the formula:

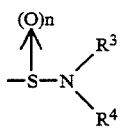

and n is 1 or 2, or its salt can be produced by, for example, subjecting a compound represented by the formula (VI):

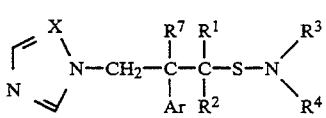

wherein the symbols have the same meanings as defined above, to an oxidation.

The oxidation can be allowed to proceed, usually, in water or an organic solvent such as ketones (e.g., acetone or methylethylketone), alcohols (e.g., methanol, ethanol, propanol, isopropanol or butanol), esters (e.g., ethyl acetate or methyl acetate), hydrocarbons (e.g., benzene toluene, hexane, xylene or petroleum benzine), nitriles (e.g., acetonitrile), halogenated hydrocarbons (e.g., dichloromethane), amides (e.g., N,N-dimethylformamide or dimethylacetamide), singly or in a mixture thereof, while keeping the reaction system at a temperature ranging from about $-20°$ C. to about $+100°$ C. The reaction time is about 30 minutes to 24 hours. The amount of water or other organic solvent to be used is about 5 to 100 equivalents to 1 mol of the compound (VI). In this oxidation reaction, an oxidizing agent (e.g., potassium permanganate, hydrogen peroxide or m-chloroperbenzoic acid) can be used. In this oxidation reaction, a compound of formula (I), wherein n is 1 or 2, can be obtained independently or as a mixture thereof by selecting the kinds of the oxidizing agents and controlling the equivalent relative to the compound of formula (VI) and reaction conditions (e.g., temperature, solvent and reaction time).

A compound of formula (I), wherein B is a group of the formula:

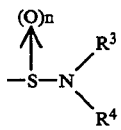

and n is 2, can be produced by, for example, reacting a compound of formula (VII):

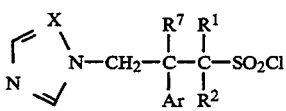 (VII)

wherein the symbols have the same meanings as defined above, or its salt with a compound of formula (III).

The reaction can be allowed to proceed, usually, in water or an organic solvent such as ketones (e.g., acetone or methylethylketone), alcohols (e.g., methanol, ethanol, propanol, isopropanol or butanol), esters (e.g., ethyl acetate, methyl acetate), hydrocarbons (e.g., benzene, toluene, hexane, xylene or petroleum benzine), nitriles (.e.g., acetonitrile), halogenated hydrocarbons (e.g., dichloromethane), amides (e.g., N,N-dimethylformamide or dimethylacetamide), singly or in a mixture thereof while keeping the reaction system at a temperature ranging from about $-20°$ C. to about $+100°$ C. The reaction time is about 30 minutes to 24 hours. The amount of water or other organic solvent to be used is about 5 to 100 equivalents to 1 mol of the compound (VII). In this case, for the purpose of accelerating the reaction, a base such as triethylamine, pyridine, p-dimethylaminopyridine, potassium carbonate, sodium hydrogencarbonate or sodium carbonate can be allowed to coexist in the reaction system.

A compound of formula (I), wherein B is a group of the formula:

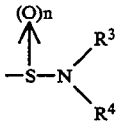

and $R^7$ forms a bond together with $R^1$, or its salt, namely, a compound of formula (I') wherein B is a group of the formula:

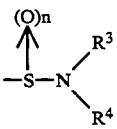

can be produced by reacting a compound of formula (VIII):

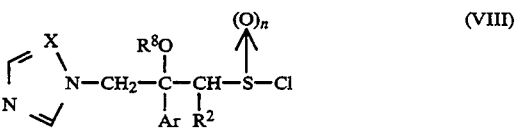 (VIII)

wherein $R^8$ is a hydrogen atom or acyl group, and the other symbols have the same meanings as define above, or its salt, with a compound of formula (III).

The reaction can be allowed to proceed, usually, in water or an organic solvent such as ketones (e.g., acetone or methylethylketone), alcohols (e.g., methanol, ethanol, propanol, isopropanol or butanol), esters (e.g., ethyl acetate or methyl acetate), hydrocarbons (e.g., benzene, toluene, hexane, xylene or petroleum benzine), nitriles (e.g., acetonitrile), halogenated hydrocarbons (e.g., dichloromethane), amides (e.g., N,N-dimethylformamide or dimethylacetamide), singly or in a mixture thereof, while keeping the reaction system at a temperature ranging from about $-20°$ C. to about $+100°$ C. The reaction time is about 30 minutes to 24 hours. The amount of water or other organic solvent to be used is about 5 to 100 equivalents to 1 mol of the compound (VIII). In this case, for the purpose of accelerating the reaction rate, a base such as triethylamine, pyridine, 4-dimethylaminopyridine or picoline can be allowed to coexist in the reaction system.

A compound of formula (I), wherein $R^7$ is an acylated hydroxyl group, or its salt, can also be produced by, for example, reacting a compound of formula (IX):

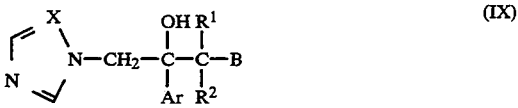 (IX)

wherein the symbols have the same meanings as defined above, with a compound of formula (Xa):

$R^{8a}$—W (Xa)

wherein $R^{8a}$ is an acyl group and W is a halogen (e.g., chlorine or bromine) or the formula $OR^{8b}$ (wherein $R^{8b}$ is an acyl group (e.g., acetyl or propionyl)).

The reaction can be allowed to proceed, usually, in water or an organic solvent such as ketones (e.g., acetone or methylethylketone), alcohols (e.g., methanol, ethanol, propanol, isopropanol or butanol), esters (e.g., ethyl acetate or methyl acetate), hydrocarbons (e.g., benzene, toluene, hexane, xylene or petroleum benzine), nitriles (e.g., acetonitrile), halogenated hydrocarbons (e.g., dichloromethane), amides (e.g., N,N-dimethylformamide or dimethylacetamide), singly or in a mixture thereof, while keeping the reaction system at a temperature ranging from about $-20°$ C. to about $+100°$ C. The reaction time is about 30 minutes to 24 hours. The amount of water or other organic solvent to be used is about 5 to 100 equivalents to 1 mol of the compound (IX). In this case, for the purpose of accelerating the reaction rate, a base such as triethylamine, pyridine, 4-dimethylaminopyridine or picoline can be allowed to coexist in the reaction system.

A compound of formula (I), wherein both $R^1$ and $R^7$ are a hydrogen atom, or its salt, can also be produced by, for example, subjecting a compound of formula (I') to catalytic reduction. The reaction can be allowed to proceed, usually, in water or an organic solvent such as ketones (e.g., acetone or methylethylketone), alcohols (e.g., methanol, ethanol, propanol, isopropanol or butanol), esters (e.g., ethyl acetate or methyl acetate), hydrocarbons (e.g., benzene, toluene, hexane, xylene or petroleum benzine), nitriles (e.g., acetonitrile), halogenated hydrocarbons (e.g., dichloromethane), amides (e.g., N,N-dimethylformamide or dimethylacetamide), singly or in a mixture thereof, in the presence of a suitable metal catalyst, for example, palladium-carbon. This reduction can be conducted under atmospheric pressure or an elevated pressure up to about 150 kg/cm² at a temperature from ordinary temperature to about +100° C.

A compound of formula (I), wherein B is a group of the formula:

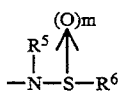

or its salt, can be Produced by, for example, reacting a compound of formula (IV):

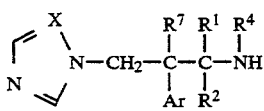     (IV)

wherein the symbols have the same meanings as defined above, or its salt, with a compound of formula (V):

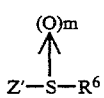     (V)

wherein the symbols have the same meanings as defined above, and Z' has the same meaning for Z.

The group represented by Z' in the compound of formula (V) is an active group which is removed by the reaction with the amine (IV). Although a halogen atom such as a chlorine atom is preferable for Z', specific limitation should not be made therefor.

The reaction can be allowed to proceed, usually, in water or an organic solvent such as ketone (e.g., acetone, methylethylketone), alcohols (e.g., methanol, ethanol, propanol, isopropanol or butanol), esters (e.g., ethyl acetate or methyl acetate), hydrocarbons (e.g., benzene, toluene, hexane, xylene or petroleum benzine, nitriles (e.g., acetonitrile), halogenated hydrocarbons (e.g., dichloromethane), amides (e.g., N,N-dimethylformamide or dimethylacetamide), singly or in a mixture thereof, while keeping the reaction system at a temperature ranging from about −20° C. to about +100° C. The reaction time is about 30 minutes to 24 hours. The amount of water or other organic solvent to be used is about 5 to 100 equivalents to 1 mol of the compound (IV). In this case, for the purpose of accelerating the reaction rate, a base such as triethylamine, pyridine, 4-dimethylaminopyridine or picoline can be allowed to coexist in the reaction system.

A of formula (I), wherein B is a group of the formula:

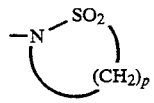

wherein p denotes an integer of 2 to 5, or its salt, can be obtained by processing, for example, a compound of formula (XI):

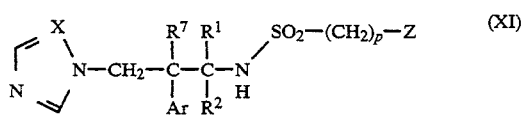     (XI)

wherein the symbols have the same meanings as defined above, or its salt, with a base.

The reaction can be allowed to proceed, usually, in water or an organic solvent such as ketones (e.g., acetone or methylethylketone), alcohols (e.g., methanol, ethanol, propanol, isopropanol or butanol), esters (e.g., ethyl acetate or methyl acetate), hydrocarbons (e.g., benzene, toluene, hexane, xylene or petroleum benzine), nitriles (e.g., acetonitrile ), halogenated hydrocarbons (e.g., dichloromethane), amides (e.g., N,N-dimethylformamide or dimethylacetamide), singly or in a mixture thereof, while keeping the reaction system at a temperature ranging from about −20° C. to about +100° C. The reaction time is about 30 minutes to 24 hours. The amount of water or other organic solvent to be is about 5 to 100 equivalents to 1 mol of the compound (XI). Examples of the bases to be employed include sodium methylate, sodium, potassium tert-butylate and sodium hydroxide.

A compound of formula (I), wherein B is a group of the formula:

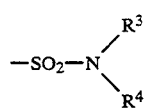

wherein the symbols have the same meanings as defined above, or a group of the formula:

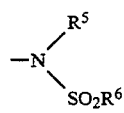

wherein the symbols have the same meanings as defined above, or its salt, can be prepared by reacting, for example, a Compound of formula (Id):

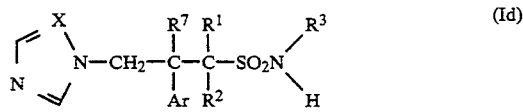     (Id)

wherein the symbols have the same meanings as defined above, or a compound of formula (Ie):

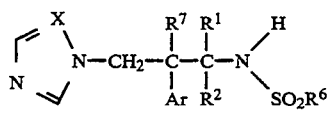

wherein the symbols have the same meanings as defined above, with a compound of formula (Xb):

$$R^{4'}-W^a \quad (Xb)$$

wherein $R^{4'}$ has the same meaning as $R^4$ or $R^5$, $W^a$ is a halogen atom (e.g., chlorine, bromine or iodine) or a group represented by $R^{10}SO_3$- (wherein $R^{10}$ is a lower ($C_{1-4}$) alkyl, trifluoromethyl, phenyl or tolyl).

The reaction can be allowed to proceed, usually, in water or an organic solvent such as ketones (e.g., acetone or methylethylketone), alcohols (e.g., methanol, ethanol, propanel, isopropanol or butanol), esters (e.g., ethyl acetate or methyl acetate), hydrocarbons (e.g., benzene, toluene, hexane, xylene or petroleum benzine), nitriles (e.g., acetonitrile), halogenated hydrocarbons (e.g., dichloromethane), amides (e.g., N,N-dimethylformamide or dimethylacetamide), singly or in a mixture thereof, while keeping the reaction system at a temperature ranging from about −20° C. to about +100° C. The reaction time is about 30 minutes to 24 hours. The amount of water or other organic solvent to be used is about 5 to 100 equivalents to 1 mol of the compound (Id) or (Ie). In this case, for the purpose of accelerating the reaction rate, a base such as sodium methylate, sodium ethylate, sodium hydroxide, potassium hydroxide, sodium carbonate, potassium carbonate, sodium hydrogencarbonate or sodium hydride can be allowed to coexist in the reaction system.

A compound of formula (I), wherein B is a group of the formula:

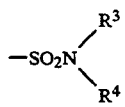

wherein the group of

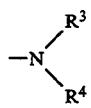

is N-substituted piperazine, or its salt, can be produced by, for example, reacting a compound of formula (If):

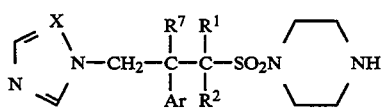

wherein the symbols have the same meanings as defined above, or its salt, with the compound of formula (Xa), (Xb) or its salt.

The reaction can be allowed to proceed, usually, in water or an organic solvent such as ketones (e.g., acetone or methylethylketone), alcohols (e.g., methanol, ethanol, propanol, isopropanol or butanol), esters (e.g., ethyl acetate or methyl acetate), hydrocarbons (e.g., benzene, toluene, hexane, xylene or petroleum benzine), nitriles (e.g., acetonitrile), halogenated hydrocarbons (e.g., dichloromethane), amides (e.g., N,N-dimethylformamide or dimethylacetamide), singly or in a mixture thereof, while keeping the reaction system at a temperature ranging from about −20° C. to about +100° C. The reaction time is about 30 minutes to 24 hours. The amount of water or other organic solvent to be used is about 5 to 100 equivalents to 1 mol of the compound (If). In this case, for the purpose of accelerating the reaction, a base such as sodium methylate, sodium ethylate, sodium hydroxide, potassium hydroxide, sodium carbonate, potassium carbonate, sodium hydrogencarbonate, sodium hydride, triethylamine, pyridine, dimethylaminopyridine, ethyldiisopropylamine can be allowed to coexist in the reaction system.

A compound of formula (I), wherein B is $SO_2NH_2$, or its salt, can be produced by, for example, subjecting a compound of formula (Ig):

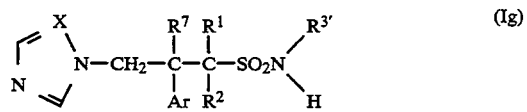

wherein $R_{3'}$ is an aralkyl group (e.g., benzyl, 4-methoxybenzyl, 3,4-dimethoxybenzyl, 3,4,5-trimethoxybenzyl or benzhydryl) and the other symbols have the same meanings as defined above, to removal for protecting group.

The reaction can be allowed to proceed, usually, in water or an organic solvent such as ketones (e.g., acetone or methylethylketone), alcohols (e.g., methanol, ethanol, propanol, isopropanol or butanol), esters (e.g., ethyl acetate or methyl acetate), hydrocarbons (e.g., benzene, toluene, hexane, xylene or petroleum benzine), nitriles (e.g., acetonitrile), halogenated hydrocarbons (e.g., dichloromethane), amides (e.g., N ,N-dimethylformamide or dimethylacetamide), singly or in a mixture thereof, and acid (e.g., sulfuric acid, trifluoroacetate or p-toluenesulfonate) while keeping the reaction system at a temperature ranging from about 0° C. to about +150° C. The reaction time is about 30 minutes to 24 hours. The amount of water, other organic solvent or acid to be used is about 5 to 100 equivalents to 1 mol of the compound (Ig).

In the intermediate compound of formula (II) wherein Z is chlorine, i.e. the compound of formula (II'), can be produced by, for example, the method shown by the following reaction scheme.

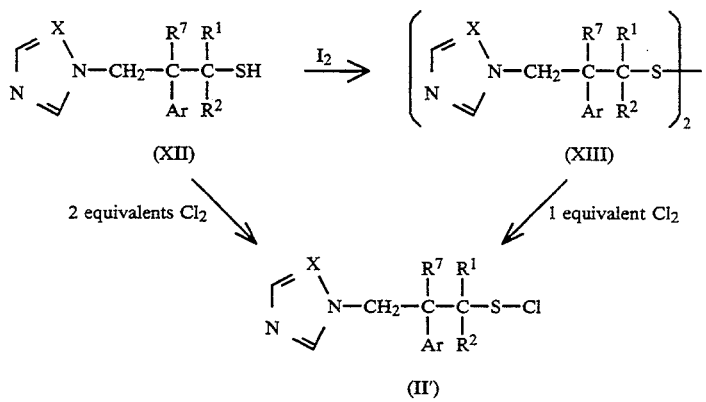

wherein the symbols have the same meanings as defined above.

Preferable examples of the solvents to be employed for the oxidation (XII→II′ and XIII→II′) with chlorine in the above method include chloroform, dichloromethane and carbon tetrachloride.

The intermediate compound of formula (VII) can be produced by, for example, the following reaction scheme.

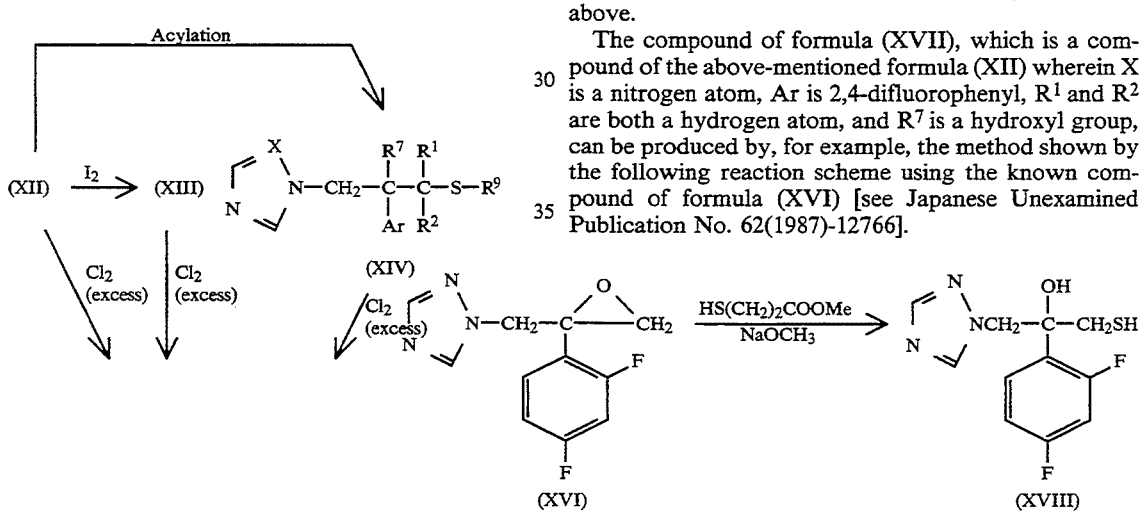

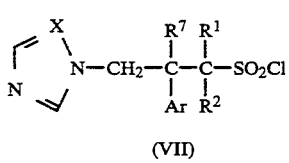

(VII)

wherein $R^9$ is an acyl group, and the other symbols have the same meanings as defined above.

Preferable examples of the solvents to be employed in the oxidation reaction by chlorine in the manufacture of the present invention (XII→VII, XIII→VII and XIV→VII) include water, acetic acid, a mixture thereof and a mixture of acetic acid and carbon tetrachloride.

The above-mentioned oxidation reaction using the intermediate compound of formula (XII), (XIII) or (XIV), wherein $R^7$ is $OR^8$ and $R^1$ is hydrogen can produce a compound of formula (XV), which is an intermediate compound of formula (VIII), wherein n is 2.

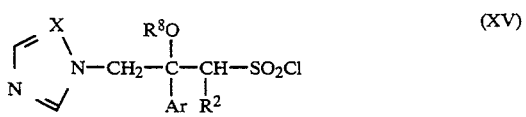

wherein the symbols have the same meanings as defined above.

The compound of formula (XVII), which is a compound of the above-mentioned formula (XII) wherein X is a nitrogen atom, Ar is 2,4-difluorophenyl, $R^1$ and $R^2$ are both a hydrogen atom, and $R^7$ is a hydroxyl group, can be produced by, for example, the method shown by the following reaction scheme using the known compound of formula (XVI) [see Japanese Unexamined Publication No. 62(1987)-12766].

The compound of formula (XX), which is a compound of the above-mentioned formula (XII) wherein X is a nitrogen, Ar is 2,4-difulorophenyl, $R^1$ is methyl and $R^2$ is hydrogen, can be produced by, for example, the method shown by the following reaction scheme using the known compound of formula (XVIII) [see Abstract of Papers, The 8th Medicinal Chemistry Symposium, p.9, held in Osaka, 1986].

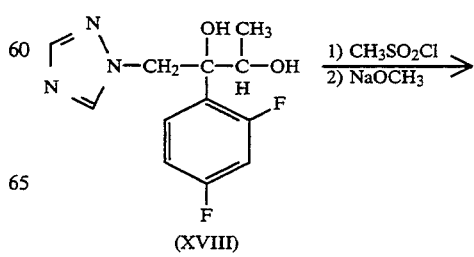

(XVIII)

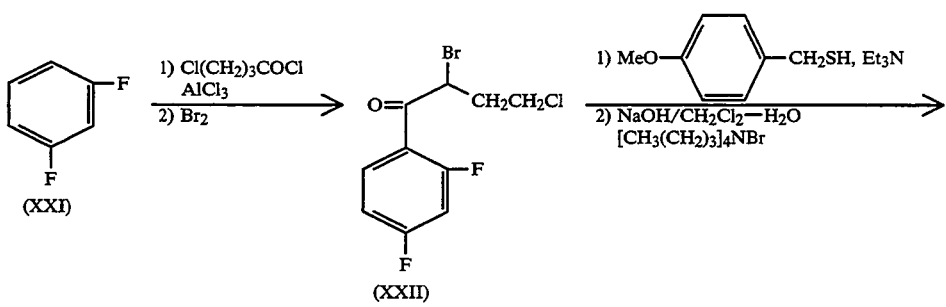

The compound of formula (XXVI), which is a compound of the above-mentioned formula (XII) wherein Ar is 2,4-difluorophenyl, $R^1$ is linked with $R^2$ to form ethylene, and $R^7$ is a hydroxyl group, can be produced by, for example, the method shown by the following reaction scheme.

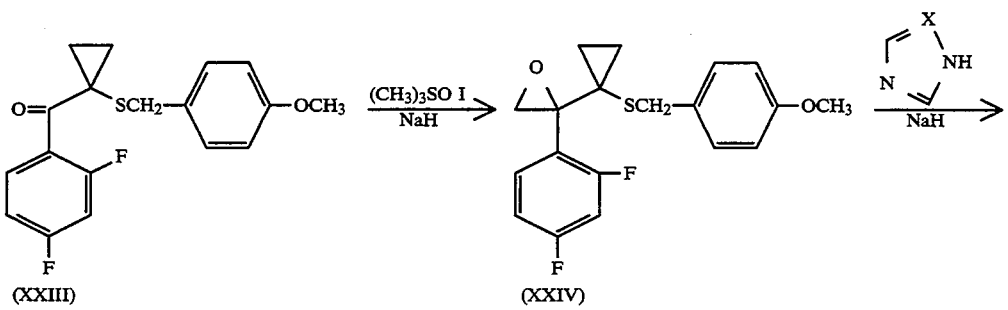

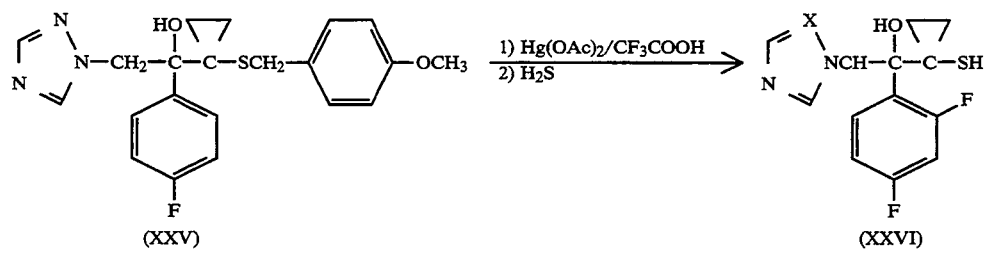

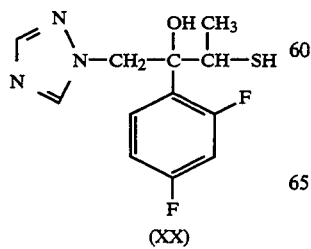

The compound of formula (XXXIII), which is a compound of the above-mentioned formula (XII) wherein Ar is 2,4-difluorophenyl, $R^1$ and $R^2$ are both methyl, and $R^7$ is a hydroxyl group, can be produced by, for example, the following reaction scheme.

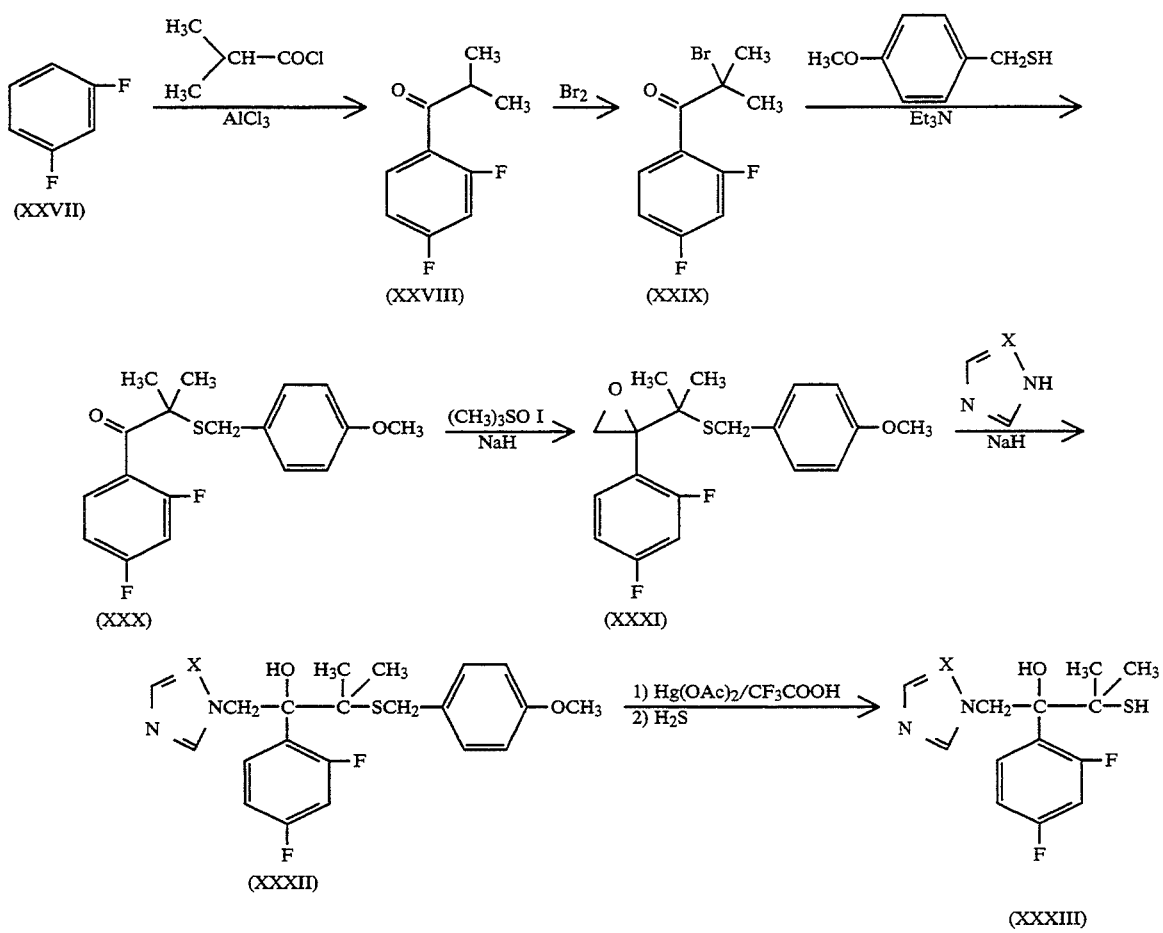

The compound, which is an intermediate compound of formula (IV) wherein X is a nitrogen atom, Ar is 2,4-difluorophenyl, $R^1$, $R^2$ and $R^5$ are all hydrogen and $R^7$ is a hydroxyl group, can be produced by the method described in Japanese Unexamined Patent Publication No. 63(1988)-45672.

The compound, which is an intermediate compound of formula (IV) wherein X is a nitrogen atom, Ar is 2,4-difluorophenyl, $R^1$ is hydrogen, $R^2$ and $R^5$ are both methyl, and $R^7$ is a hydroxyl group, can be produced by, for example, the method described in Japanese Unexamined Patent Publication No. 2(1990)-191262.

As the compound of formula (I) or its salt has, in its molecule, one or more asymmetric atoms or a double bond which generates a cis-trans isomer, at least two stereoisomers exist, and these stereoisomers and a mixture thereof are all included in the present invention. In particular, when $R^1$ is a hydrogen atom, $R^2$ is methyl and $R^7$ is an acylated hydroxyl group, an optically active compound, wherein the carbon to which the substituted phenyl group shown by Ar and the carbon to which $R^2$ is bonded are both R-configurated, is preferable.

The compound of formula (I) can also be obtained as a salt. Examples of the salts include inorganic acid salts such as hydrochloride, hydrobromide, sulfate, nitrate or phosphate; organic acid salts such as formate, acetate, trifluoroactate, tartarate, citrate, fumarate, maleate, toluenesulfonate or methanesulfonate; alkaline metal salts such as sodium salt or potassium salt; alkaline metal salts such as calcium salt; alkaline earth metal salts such as magnesium salt; metal salts such as aluminum salt; inorganic base salts such as ammonium salt or hydrazine salt; and nitrogen-containing organic base salts such as triethylamine salt or guanidine salt, quinine salt or cinchonine salt.

The salts of the compounds (II) to (XI) are the same as those of the compound (I).

The resultant compound formula (I) or its salt can be isolated from the reaction mixture by a conventional isolation and purification procedure such as extraction, concentration, neutralization, filtration, recrystallization, column chromatography and thin-layer chromatography.

The compound formula (I) or its salt may exist as at least two stereoisomers. These isomers as well as a mixture thereof are subsumed in the concept of the present invention and, when desired, can be individually produced. For example, by subjecting a specific isomer of the starting compounds of formula (Id), (Ie), (If), (Ig), (II), (III), (IV), (V), (VI), (VII), (VIII), (IX), (Xa), (Xb) and (XI) to the corresponding reaction described hereinbefore, the corresponding isomer of the compound of formula (I) can be selectively produced. On the other hand, when the reaction product is a mixture of two or more isomers, it can be fractionated into respective isomers by conventional fractionation techniques such as formation of a salt with an optically active acid (e.g., camphorsulfonic acid or tartaric acid), several types of chromatography, fractional recrystallization and so on.

The compound of formula (I) or salt thereof can be converted to the corresponding physiologically acceptable salt, by using one of the aforementioned inorganic acids or organic acids. Further, the salt of the compound of formula (I) can be subjected to salt exchange reaction to be changed to a desired other salt.

Activity

Evaluation of the antifungal activities of the compound of formula (I) was conducted by the following method: a sheet of filter paper disc (manufactured by Toyo Seisakusho, 8 mm in diameter) soaked in a 1000 μ/ml solution of a compound of formula (I) in methanol was placed on an agar plate containing various fungi, which was incubated at 28° C. for two days, and the diameter of the growth inhibition zone around the filter paper disc was measured. The following culture media were used: A: yeast nitrogen base agar medium (pH 7.0) B: Sabouraud agar medium The antifungal spectra of the compounds of formula (I) are shown in Table 4.

TABLE 4

Antifungal spectrum

| Test microorganism | Medium | Diameter of growth inhibition zone (mm) | | |
|---|---|---|---|---|
| | | cpd. 2 | cpd. 21 | cpd. 23 |
| Candida albicans IFO 0583 | A | 25 | 43 | 45 |
| Candida utilis IFO 0619 | A | 36 | 40 | 45 |
| Aspergillus niger IFO 4066 | A | 25 | 20 | 20 |
| Aspergillus fumigatus IFO 6344 | A | 25 | 30 | 22 |
| Cryptococcus neoformans IFO 0410 | A | 38 | 30 | 40 |
| Trichophyton rubrum IFO 6467 | B | 35 | 45 | 40 |
| Trichophyton mentagrophytes IFO 7522 | B | 25 | 25 | 25 |
| Microsporum gypseum IFO 6075 | B | 22 | 24 | 30 |

The antifungal activities of the compound of formula (I) against Candida albicans are shown in Table 5.

TABLE 5

| cpd. No. | Diameter of growth-inhiibition zone (mm) Candida . albicans (IFO 0583) (Medium A, 28° C., two-day culture) |
|---|---|
| 4 | 40 |
| 5 | 35 |
| 6 | 40 |
| 7 | 33 |
| 8 | 40 |
| 10 | 35 |
| 12 | 37 |
| 14 | 38 |
| 16 | 40 |
| 17 | 40 |
| 18 | 37 |
| 19 | 40 |
| 20 | 22 |
| 22 | 30 |
| 24 | 37 |
| 25 | 30 |
| 26 | 20 |
| 28 | 50 |
| 30 | 12 |
| 31 | 35 |
| 32 | 12 |
| 34 | 15 |
| 35 | 30 |
| 39 | 40 |
| 41 | 23 |
| 42 | 40 |

TABLE 5-continued

| cpd. No. | Diameter of growth-inhiibition zone (mm) Candida . albicans (IFO 0583) (Medium A, 28° C., two-day culture) |
|---|---|
| 43 | 35 |
| 44 | 33 |
| 45 | 50 |
| 46 | 45 |
| 47 | 45 |
| 48 | 48 |
| 49 | 30 |
| 50 | 45 |
| 51 | 38 |
| 52 | 35 |
| 53 | 40 |
| 54 | 40 |
| 55 | 35 |
| 56 | 30 |
| 57 | 35 |
| 58 | 40 |
| 59 | 30 |
| 60 | 35 |
| 61 | 18 |
| 62 | 45 |
| 63 | 40 |
| 64 | 40 |
| 65 | 30 |
| 66 | 42 |
| 67 | 42 |
| 68 | 42 |
| 69 | 42 |
| 70 | 42 |
| 71 | 47 |
| 72 | 48 |
| 73 | 32 |
| 74 | 44 |
| 75 | 34 |
| 76 | 40 |
| 77 | 40 |
| 78 | 40 |
| 79 | 30 |
| 80 | 40 |
| 81 | 40 |
| 82 | 40 |
| 83 | 40 |
| 84 | 23 |
| 85 | 45 |
| 86 | 35 |
| 87 | 38 |
| 88 | 46 |
| 89 | 35 |
| 90 | 40 |
| 91 | 50 |
| 92 | 53 |

The protective effects of compound of formula (I) against Candida albicans infection in mice are shown in Table 6.

Test Method: Five-week old Crj:CDF$_1$ mice were inoculated with the minimum lethal dose of Candida albicans intravenously. The test drug was given once immediately after infection. The effectiveness of the drug was expressed in ED$_{50}$ values calculated by the Reed and Muench method from the survival rate 7 days after infection.

TABLE 6

| cpd. No. | ED$_{50}$ (mg/kg) |
|---|---|
| 2 | 5.0 (po), 5.0 (sc) |
| 4 | 7.07 (po) |
| 6 | 7.07 (po) |
| 8 | 20.0 (po), 28.3 (sc) |
| 10 | 7.07 (po), 14.1 (sc) |
| 12 | 5.0 (po) |
| 14 | 5.0 (po) |
| 16 | 5.0 (po) |
| 23 | 7.1 (po) |
| 35 | 20.0 (po) |
| 39 | 8.0 (po) |

TABLE 6-continued

| cpd. No. | ED$_{50}$ (mg/kg) |
|---|---|
| 46 | 8.0 (po) |
| 48 | 11.3 (po) |
| 49 | 1.8 (po) |
| 51 | 8.0 (po) |
| 53 | 3.5 (po) |
| 54 | 3.5 (po) |
| 55 | 2.0 (po) |
| 58 | 8.0 (po) |
| 59 | 11.3 (po) |
| 64 | 2.8 (po) |
| 65 | 11.3 (po) |
| 70 | 8.0 (po) |
| 71 | 8.0 (po) |
| 73 | 6.4 (po) |
| 75 | 8.0 (po) |
| 76 | 8.0 (po) |
| 78 | 8.0 (po) |
| 86 | 8.0 (po) |
| 91 | 11.3 (po) | sc: Subcutaneous administration
po: Oral administration

The compounds of this invention and salts thereof, having low toxicities and high antifungal activities with broad antifungal spectra as shown above, can be used for prevention and treatment of fungal infections in human beings, domestic animals and fowls. The compounds of this invention and salts thereof can also be used as antifungal preparations for agricultural use.

The compound (I) or its salt can safely be administered to human beings, orally or parenterally, in per se or in the form of a pharmaceutically acceptable composition in admixtures with a pharmaceutically acceptable carrier, excipient or diluent. A daily dosage of the present compound is not specifically limited, since it depends upon the state of the infection, age, sex, weight and sensitivity of a patient, administration route, period and interval for administration and types of active ingredients. In the case of the oral dose for treatment of Candida infection for an adult, the daily dosage lies in a range of about 0.1 to 100 mg/Kg per day, preferably about 1 to 50 mg/Kg per day. The present compound can be parenterally administered as an ointment containing the compound (I) in an amount of about 0.1 to 100 mg per 1 g.

Examples of the oral administration preparations are powders, granules, pellets, capsules, sublingual tablets or the like, while examples of the parenteral administration preparations are ointments, lotion, injections, pessaries or the like. These preparations can be formulated by using a pharmaceutically acceptable solid or liquid carrier, excipient or diluent in accordance with a conventional method. Further, these preparations can also be prepared by optionally adding a binding agent, disintegrating agent, lubricant, coloring agent, flavour, solubilizer, stabilizing agent or the like.

The compounds of the invention or, salt thereof can also be used as an antifungal preparations for agricultural use which is used such that the amount of the compound (I) or its salt is about 3 to 300 g per 10 ares, preferably about 10 to 100 g per ares. The preparation may contain the active ingredient of 10 to 100 ppm. Further, the preparation may be directly sprayed or drenched to plant. The amount, concentration or method to be used may be changed for a safe and effective application to plants.

Examples of the preparations include emulsion, oil solution, nebula, water dispersible powders, powders, tablet or the like. These preparations can be formulated in accordance with a conventional method by dissolving or dispersing in a suitable liquid carrier, or mixing with or being adsorbing to a suitable solid carrier. These preparations may various additives (e.g., emulsifying agent, suspending agent, spreader, penerating agent, wetting agent, mucilage, stabilizing agent or the like).

Examples of the liquid carriers to be used are water, alcohols (e.g., methyl alcohol, ethyl alcohol, n-propyl alcohol, isopropyl alcohol or ethylene glycol), ethers (e.g., dioxane or tetrahydrofuran), aliphatic hydrocarbons (e.g., kerosene or fuel oil), aromatic hydrocarbons (e.g., benzene or toluene), halogenated hydrocarbons (e.g., methylene chloride or chloroform), acid amides (e.g., dimethylformamide or dimethylacetoamide), esters (e.g., ethyl acetate or butyl acetate), nitriles (e.g., acetonitrile or propionitrile). These carriers can be used singly or as a mixture thereof in which two or more carriers are mixed in a suitable ratio.

Examples of the solid carriers are vegetable powders (e.g., soybean flour, tobacco flour or wheat flour), mineral powders (e.g., kaolin or bentonite), alumina, sulfur powders, activated charcoals or the like. These carriers may be used singly or as a mixture thereof in which two or more carriers are mixed in a suitable ratio.

The concentration of the compound (I) or its salt in emulsion, water dispersible powders or the like is about 1 to 80 wt. %. The concentration of the compound (I) or its salt in oil solution or powders is about 0.1 to 10 wt. %. The concentration of the compound (I) or its salt in the granules or the like is about 5 to 50 wt. %. These concentrations can be changed depending upon the purpose of the use.

The present invention will be explained herebelow with reference to the following Reference Examples, Working Examples and Preparations.

The ratio of the solvent in the chromatography is a volume ratio. The symbol "%" represents parts by weight if not specified.

Reference Example 1

A mixture of (RS)-1-(2,4-difluorophenyl)-1-(1-mercaptocyclopropyl)-2-(1H-1,2,4-triazol-1-yl)ethanol (300 mg), acetic anhydride (2.5 ml), pyridine (2.5 ml) and 4-dimethylaminopyridine (122 mg) was heated for 20 hours at 80° C. The reaction mixture was concentrated to dryness. To the concentrate was added ethyl acetate to filter off the insolubles. The filtrate was washed with water and a saturated aqueous saline solution, which was dried and then concentrated. The concentrate was subjected to a silica gel column chromatography for purification. Desired fractions were combined and concentrated, followed by recrystallization from ethyl acetate-isopropyl ether to give (RS)-1-(1-acetylthiocyclopropyl)-1-(2,4-difluorophenyl)-2-(1H,1,2,4-triazol-1-yl)ethyl acetate (320 mg) as pale yellow prisms.

This product (200 mg) was dispersed in a 50% aqueous solution of acetic acid (8 ml), to which chlorine gas was introduced for two hours under ice-cooling. The reaction mixture was concentrated under reduced pressure, to which ethyl acetate was added, followed by cooling. Crystalline precipitates were collected by filtration to afford (RS)-1-(1-chlorosulfonylcyclopropyl)-1-(2,4-difluorophenyl)-2-(1H-1,2,4-triazol-1-yl)ethyl acetate (200 mg) as colorless crystals.

m.p. 163°–165° C. IR$\nu$ cm (KBr): 1755, 1610, 1500,, 1425, 1375, 1210 $^1$H-NMR(DMSO-d$_6$) $\delta$: 0.50–0.70 (1H,m), 1.40–2.20 (3H,m), 2.09 (3H,s), 5.39 (1H,d,J=15

Hz), 5.83 (1H,d,J=15 Hz), 7.15–7.45 (2H,m), 7.80 (1H,m), 8.11 (1H,s), 8.45 (1H,s)

Reference Example 2

A mixture of (2R,3R)-2-(2,4-difluorophenyl)-3-mercapto-1-(1H-1,2,4-triazol-1-yl)-2-butanol (10 g), acetic anhydride (50 mg), pyridine (100 ml) and 4-dimethylamino pyridine (4.26 g) was heated for 24 hours at 80° C. The reaction mixture was concentrated to dryness, to which ethyl acetate was added to filter off the insolubles.

The filtrate was washed with water and a saturated aqueous saline solution, which was dried and then concentrated. The concentrate was subjected to a silica-gel chromatography for purification to give (2R,3R)-3-acetylthio-2-(2,4-difluorophenyl)-1-(1H-1,2,4-triazol-1-yl)-2-butyl acetate as a pale yellow solid.

This product was dissolved in a 50% aqueous solution of acetic acid (150 ml), to which chlorine gas was introduced for 3 hours under ice-cooling. The reaction mixture was concentrated under reduced pressure. The concentrate was dissolved in ethyl acetate (150 ml), which was washed with water and an aqueous solution of sodium hydrogencarbonate, then dried and concentrated to give (2R,3R)-3-chlorosulfonyl-2-(2,4-difluorophenyl)-1-(1H-1,2,4-triazol-1-yl)- 2-butyl acetate (7.6 g) as a pale brown solid matter.

m.p. 110°–115° C. IR$\nu$ cm$^{-1}$(KBr): 1760, 1615, 1500, 1365, 1220, 1165 $^1$H-NMR (CDCl$_3$) $\delta$: 1.90 (3H,dd,J=7 Hz, J=2.6 Hz), 2.16 (3H,s), 5.15 (1H,q,J=7 Hz), 5.36 (1H,d,J=15 Hz), 5.45 (1H, dd,J=15 Hz, J=2.2 Hz), 6.85–7.00 (2H,m), 7.40 (1H,m), 7.92 (1H,s), 7.94 (1H,s)

Working Example 1

Bis [(2R, 3R)-3-(2,4-difluorophenyl)-3-hydroxy-4-(1H-1,2,4-triazol-1-yl)-2-butyl]disulfide (0.73 g) was dissolved in dichloromethane (15 ml). To the solution was added, under ice-cooling, a carbon tetrachloride solution (1.6 ml) containing chlorine (0.11 g). The reaction mixture was stirred for one hour under ice-cooling, which was then added to a toluene solution of dimethylamine (20% solution, 1.45 ml). The mixture was stirred for 30 minutes under ice-cooling. The reaction mixture was washed with water and dried (MgSO$_4$), then the solvent was distilled off to leave N,N-dimethyl-[(2R,3R)-3-(2,4-difluorophenyl)-3-hydroxy-4-(1H-1,2,4-triazol-1-yl)-2-butane]sulfenamide (Compound 1) as a crude product.

This product was dissolved in acetone (40 ml), to which a saturated aqueous solution of potassium permanganate (3 ml) was added dropwise. Precipitates were filtered off, and the filtrate was concentrated under reduced pressure. The concentrate was, dissolved in ethyl acetate. The solution was washed with water, dried and concentrated. The concentrate was subjected to a silica gel chromatography (eluent: hexane/ethyl acetate=$\frac{1}{2}$) for purification, followed by recrystallization from ethyl acetate-isopropyl ether to give N,N-dimethyl-[(2R,3R)-3-(2,4-difluorophenyl)-3-hydroxy-4-(1H-1,2,4-triazol-1-yl) -2-butane]sulfonamide (Compound 2, 127 mg) as colorless needles.

m.p. 182°–183° C. IR$\nu$ cm$^{-1}$(KBr): 3400, 1615, 1500, 1325, 1145, 1120 $^1$H-NMR (CDCl$_3$) $\delta$: 1.16(3H,d,J=7 Hz), 3.02(6H,s), 3.88(1H,q,J=7 Hz), 4.92(1H,s), 504(1H,dd,J=14 Hz,1.4 Hz), 5.14(1H,d,J=14 Hz), 6.68–6.85(2H,m), 7.25–7.40(1H,m), 7.65(1H,s), 7.95(1H,s) Elemental Analysis for C$_{14}$H$_{18}$F$_2$N$_4$O$_3$S:

Calcd.: C, 46.66; H, 5.3; N, 15.55 Found: C, 46.59; H, 4.95; N, 15.67

Working Example 2

Bis[(2R,3R)-3-(2,4-difluorophenyl)-3-hydroxy-4-(1H-1,2,4-triazol-1-yl)-2-butyl]disulfide (0.50 g) was dissolved in dichloromethane (20 ml). To the solution was added dropwise, under ice-cooling, a carbon tetrachloride solution (0.88 ml) containing chlorine (62 mg). The mixture was stirred for 20 minutes under ice-cooling, then the reaction mixture was added to a dichloromethane solution (5 ml) of n-butylamine (0.26 g), which was stirred for 30 minutes under ice-cooling. The reaction mixture was washed with water and dried, then the solvent was distilled off to give a crude product of N-butyl-[(2R,3R)-3-(2,4-difluorophenyl)-3-hydroxy-4-(1H-1,2,4-triazol-1-yl)-2-butane]sulfenamide (Compound 3).

This crude product was dissolved in acetone (20 ml), to which a saturated aqueous solution of potassium permanganate (4 ml) was added dropwise. The reaction mixture was subjected to filtration, and the filtrate was concentrated under reduced pressure. To the residue was added ethyl acetate (30 ml) to separate into two layers. The organic layer was washed with water, then dried, which was concentrated under reduced pressure. The concentrate was purified by means of a silica gel column chromatography to give N-butyl-[(2R,3R)-3-(2,4-difluorophenyl)-3-hydroxy-4-(1H-1,2,4-triazol-1-yl)-2-butane]sulfonamide (Compound 4, 0.25 g) as a colorless oily product. This product was processed with a 4N-hydrogen chloride ethyl acetate solution to give Compound 4.hydrochloride (252 mg) as colorless powder.

m.p.146°–152° C. IR $\mu$cm$^{-1}$ (KBr): 3400, 3140, 1610, 1510, 1420, 1320, 1150, 1130

$^1$H-NMR (CDCl$_3$) $\delta$: 0.90(3H,t,J=7 Hz), 1.06(3H,d,J=7 Hz), 1.20–1.60(4H,m), 3.04(2H,m), 3.70(1H,q,J=7 Hz), 4.87(1H,d,J=14 Hz), 5.22(1H,d,J=14 Hz), 6.87(1H,m), 7.10–7.28(2H,m), 7.42(1H,NH), 7.71(1H,s), 8.56(1H,s) SIMS: 389 (MH+)

Working Example 3

Bis[(2R,3R)-3-(2,4-difluorophenyl)-3-hydroxy-4-(1H-1,2,4-triazol-1-yl)-2-butyl]disulfide (1.0 g) was dissolved in dichloromethane (20 ml). To the solution was added dropwise, under ice-cooling, a carbon tetrachloride solution of chlorine (1M solution, 2 ml). The mixture was stirred for 20 minutes under ice-cooling, then the reaction mixture was added to a dichloromethane solution (10 ml) of cyclohexylamine (0.70 g), followed by stirring for 30 minutes under ice-cooling. The reaction mixture was washed with water and dried, then concentrated to give a crude product (1.4 g) of N-cyclohexyl-[2R, 3R)-3-(2,4-difluorophenyl)-3-hydroxy-4-(1H-1,2,4-triazol-1-yl)-2-butane]sulfenamide (Compound 5). 0.4 g of this product was subjected to a silica gel chromatography (eluent: hexane/ethyl acetate=$\frac{1}{2}$) for purification to give a compound 5 (0.26 g) as a colorless resinous substance.

$^1$H-NMR (CDCl$_3$) $\delta$: 1.21(3H,d,J=7 Hz), 1.0–2.20(10H,m), 2.66(1H,m), 3.20(1H,q,J=7 Hz), 4.88(1H,dd,J=14 Hz, J=1.2 Hz), 5.10(1H,d,J=14 Hz), 6.17(1H,s), 6.68–6.84(2H,m), 7.38(1H,m), 7.70(1H,s), 7.95(1H,s)

Working Example 4

In acetone (50 ml) was dissolved the crude product (1.0 g) of N-cyclohexyl-[(2R,3R)-3-(2,4-difluorophenyl)-3-hydroxy-4-(1H-1,2,4-triazol-1-yl)-2-butane]sulfenamide (Compound 5) obtained in Working Example 3. To the solution was added dropwise a saturated aqueous solution of potassium permanganate (6.4 ml). Insolubles were filtered off, and the filtrate was concentrated under reduced pressure. The concentrate was dissolved in ethyl acetate, washed with water and a saturated aqueous saline solution, and dried, then the solvent was distilled off under reduced pressure. The residue was subjected to a silica gel chromatography (eluent: hexane/ethyl acetate =½) for purification to give N-cyclohexyl-[(2R,3R)-3-(2,4-difluorophenyl)-3-hydroxy-4-(1H-1,2,4-triazol-1-yl)-2-butane]sulfonamide (Compound 6, 0.64 g) as a colorless solid. This product was processed with hydrogen chloride, followed by recrystallization from methanol-ethyl acetate to give Compound 6.hydrochloride (0.62 g) as colorless needles.

m.p.152°–169° C. IR$\nu$ cm$^{-1}$ (KBr): 3150, 2930, 1610, 1500, 1420, 1320, 1145, 1130 $^1$H-NMR (DMSO-d$_6$) $\delta$: 1.08(3H,d,J=7 Hz), 1.15–1.95(10H,m), 3.23(1H,m), 3.67(1H,q,J=7 Hz), 4.92(1H,d,J=14 Hz), 5.25(1H,d,J=14 Hz), 6.88(1H,m), 7.10–7.30(2H,m), 7.48(1H,NH), 7.79(1H,s), 8.68(1H,s)

Working Example 5

Using bis[(2R,3R)-3-(2,4-difluorophenyl)-3-hydroxy-4-(1H-1,2,4-triazol-1-yl)-2-butyl]disulfide (1.0 g), chlorine (0.15 g) and morpholine (0.61 g), substantially the same reaction as in Working Example 3 was conducted to give N-[(2R,3R)-3-(2,4-difluorophenyl)-3-hydroxy-4-(1H-1,2,4-triazol-1-yl)-2-butylsulfenyl]morpholine (Compound 7, 0.53 g) as a colorless solid.

m.p.119°–121° C. IR$\nu$ cm$^{-1}$ (KBr): 3270, 1610, 1500, 1278, 1265, 1105 $^1$H-NMR (CDCl$_3$) $\delta$: 1.25(3H,d,J=7.4 Hz), 3.08(4H,m), 3.42(1H,q,J=7.4 Hz), 3.75(4H,m), 4.86(1H,d,J=14 Hz), 5.10(1H,d,J=14 Hz), 5.81(1H,s,OH), 6.76(2H,m), 7.39(1H,m), 7.74(1H,s), 7.88(1H,s)

Working Example 6

4-[(2R,3R) -3-(2,4-difluorophenyl) -3-hydroxy-4-(1H-1,2,4-triazol-1-yl)-2-butylsulfenyl]morpholine (Compound 7, 0.5 g) obtained in Working Example 5 was subjected to oxidation with potassium permanganate likewise in Working Example 4 to give 4-[(2R,3R)-3-(2,4-difluorophenyl)-3-hydroxy-4-(1H-1,2,4-triazol-1-yl)-2-butylsulfonyl]morpholine (Compound 8, 0.32 g) as colorless needles.

m.p.157°–158° C. IR$\nu$ cm$^{-1}$ (KBr): 3410, 1620, 1600, 1505, 1340, 1255, 1155, 1130 $^1$H-NMR (CDCl$_3$) $\delta$: 1.18(3H,d,J=7.2 Hz), 3.35–3.60(4H,m), 3.64–4.00(4H,m), 3.83(1H,q,J=7.2 Hz), 5.01(1H,dd,J=14 Hz, J=1.4 Hz), 5.04(1H,s), 5.21(1H,d,J=14 Hz), 6.68–6.85(2H,m), 7.23–7.40(2H,m), 7.70(1H,s), 7.89(1H,s) Elemental Analysis for C$_{16}$H$_{20}$F$_2$N$_4$O$_4$S: Calcd.: C, 47.75; H, 5.01; N, 13.92 Found: C, 47.87; H, 5.18; N, 14.00

Working Example 7

Using bis[(2R,3R)-3-(2,4-difluorophenyl)-3-hydroxy-4-(1H-1,2,4-triazol-1-yl)-2-butyl]disulfide (2.0 g), chlorine (0.31 g) and cyclopropylamine (0.80 g), substantially the same reaction as in Working Example 3 was allowed to proceed to give N-cyclopropyl-[(2R,3R)-3-(2,4-difluorophenyl)-3-hydroxy-4-(1H-1,2,4-triazol-1-yl)-2-butane]sulfenamide (Compound 9). This compound was subjected, likewise in Working Example 4, to oxidation with potassium permanganate to give N-cyclopropyl- [(2R,3R)-3-(2,4-difluorophenyl)-3-hydroxy-4-(1H-1,2,4-triazol-1-yl)-2-butane]sulfonamide (Compound 10) as a colorless solid substance. This product was processed with hydrogen chloride to give 10.hydrochloride (221 mg) as colorless needles.

m.p.141°–153° C. IR$\nu$ cm$^{-1}$ (KBr): 3430, 3100, 1620, 1505, 1425, 1320, 1150, 1140

$_1$H-NMR (DMSO-d$_6$) $\delta$: 0.40–0.80(4H,m), 1.09(3H,d,J=7 Hz), 2.57(1H,m), 3.86(1H,q,J=7 Hz), 4.88(1H,d,J=14 Hz), 5.30(1H,d,J=14 Hz), 6.89(1H,m), 7.10–7.30(2H,m), 7.7–7.95(1H,NH), 7.82(1H,s), 8.71(1H,s)

Working Example 8

Using bis[(2R,3R)-3-(2,4-difluorophenyl)-3-hydroxy-4-(1H-1,2,4-triazol-1-yl)-2-butyl]disulfide (2.0 g), chlorine (0.31 g) and a 40% methanol solution of dimethylamine (1.62 g), substantially the same reaction as in Working Example 3 was allowed to proceed to give a crude product of N-methyl-[(2R,3R)-3-(2,4-difluorophenyl)-3-hydroxy-4-(1H-1,2,4-triazol-1-yl)-2-butane]sulfenamide (Compound 11). This crude product was subjected, likewise in Working Example 4, to oxidation with a saturated aqueous solution of potassium permanganate (18 ml) to give N-methyl-[(2R,3R)-3-(2,4-difluorophenyl)-3-hydroxy-4(1H -1,2,4-triazol-1-yl)-2-butane]sulfonamide (Compound 12) as a colorless solid substance. This product was processed with hydrogen chloride, followed by recrystallization from methanol-ethyl acetate to give Compound 12.hydrochloride (584 mg) as colorless needles.

m.p.148°–163° C. IR$\nu$ cm$^{-1}$ (KBr): 3100, 1615, 1500, 1420, 1320, 1150, 1130

$^1$H-NMR (DMSO-d$_6$) $\delta$: 1.07(3H,d,J=7 Hz), 2.69(3H,br-s), 3.75(1H,q,J=7 Hz), 4.89(1H,d,J=14 Hz), 5.26(1H,d,J=14 Hz), 6.88(1H,m), 7.10–7.28(2H,m), 7.35(1H,m,NH), 7.84(1H,s), 8.75(1H,s)

Working Example 9

Using bis[(2R,3R)-3-(2,4-difluorophenyl)-3-hydroxy-4-(1H-1,2,4-triazol-1-yl)-2-butyl]disulfide (1.0 g), chlorine (0.15 g) and a 70% ethanol solution of ethylamine (0.46 g), substantially the same reaction as in Working Example 3 was allowed to proceed to give a crude product of N-ethyl-[(2R,3R)-3-(2,4-difluorophenyl)-3-hydroxy-4-(1H-1,2,4-triazol-1-yl)-2butane]sulfenamide (Compound 13). This product was subjected, likewise in Working Example 4, to oxidation with a saturated aqueous solution of potassium permanganate (17 ml) to give N-ethyl-[(2R,3R)-3-(2,4-difluorophenyl)-3-hydroxy-4-(1H-1,2,4-triazol-1-yl)-2-butane]sulfonamide (Compound 14) as a colorless solid substance. This product was processed with hydrogen chloride, followed by recrystallization from ethyl acetate to give Compound 14.hydrochloride (172 mg) as colorless powder. As secondary crystals, 61 mg of the hydrochloride was further obtained.

m.p.128°–140° C. IR$\nu$ cm$^{-1}$(KBr): 3125, 1615, 1500, 1420, 1320, 1155, 1135 $^1$H-NMR (DMSO-d$_6$) $\delta$: 1.07(3H,d,J=7 Hz), 1.12(3H,t,J=7 Hz), 3.09(2H,m), 3.70(1H,q,J=7 Hz), 4.88(1H,d,J=14 Hz), 5.24(1H,d,J=14 Hz), 6.87(1H,m), 7.10–7.30(2H,m), 7.45(1H,m,NH), 7.76(1H,s), 8.63(1H,s)

Working Example 10

Using bis[(2R,3R)-3-(2,4-difluorophenyl)-3-hydroxy-4-(1H-1,2,4-triazol-1-yl)-2butyl]disulfide (1.0 g), chlorine (0.15 g) and n-propylamine (0.42 g), substantially the same reaction as in Working Example 3 was allowed to proceed to give a crude product of N-propyl-[(2R,3R)-3-(2,4-difluorophenyl)-3-hydroxy-4(1H-1,2,4-triazol-1-yl)-2-butane]sulfenamide (Compound 15). This product was subjected, likewise in Working Example 4, to oxidation with a saturated aqueous'solution of potassium permanganate (16 ml) to give N-propyl-[(2R,3R)-3-(2,4-difluorophenyl)-3-hydroxy-4-(1H-1,2,4-triazol-1-yl)-2butane]sulfonamide (Compound 16) as a colorless solid substance. This product was processed with hydrogen chloride, followed by recrystallization from methanol-ethyl acetate to give Compound 16.hydrochloride (638 mg) as colorless scales.

m.p.149°-164° C. IR$\nu$ cm$^{-1}$ (KBr): 3130, 1615, 1500, 1420, 1320, 1150, 1130 $_1$H-NMR (DMSO-d$_6$) $\delta$: 0.90(3H,t,J=7 Hz), 1.07(3H,d,J=7 Hz), 1.50(2H,q,J=7 Hz), 3.01(2H,m), 3.70(1H,q,J=7 Hz), 4.89(1H,d,J=15 Hz), 5.26(1H,d,J=15 Hz), 6.88(1H,m), 7.10–7.30(2H,m), 7.46(1H,m,NH), 7.79(1H,s), 8.69(1H,s)

Working Example 11

In dichloromethane (40 ml) was dissolved bis[(2R,3R)-3-(2,4-difluorophenyl)-3-hydroxy-4-(1H-1,2,4-triazol-1-yl)-2-butyl]disulfide (3.0 g), to which was added dropwise, under ice-cooling, a carbontetrachloride solution (6.6 ml) containing chlorine (0.46 g). The reaction mixture was stirred for 5 minutes under ice-cooling, to which was added 1-tert-butoxycarbonyl piperazine (2.45 g), followed by addition of triethylamine (1.47 ml) dropwise. The reaction mixture was stirred for 15 minutes under ice-cooling, which was washed with water, dried and concentrated. The concentrate was subjected to silica gel chromatography (eluent: hexane/ethyl acetate =$\frac{1}{2}$) for purification of give N-tert-butoxycarbonyl-4-[(2R,3R)-3-(2,4-difluorophenyl)-3-hydroxy-4-(1H-1,2,4-triazol-1-yl)-2-butylsulfenyl]piperazine (Compound 17, 3.0 g) as a colorless solid substance.

m.p.116°-117° C. IR$\nu$ cm$^{-1}$ (KBr): 3170, 1710, 1618, 1500, 1420, 1130

$^1$H-NMR (CDCl$_3$) $\delta$: 1.24(3H,d,J=7 Hz), 1.47(9H,s), 3.03(4H,m), 3.41(1H,q,J=7 Hz), 3.50(4H,m), 4.85(1H,d,J=14 Hz), 5.10(1H,d,J=14 Hz), 5.72(1H,s), 6.75(2H,m), 7.37(1H,m), 7.73(1H,s), 7.87(1H,s)

Working Example 12

In acetone (50 ml) was dissolved 1-tert-butoxycarbonyl-4-[(2R,3R)-3-(2,4-difluorophenyl)-3-hydroxy-4-(1H-1,2,4-triazol-1-yl)-2-butylsulfenyl]piperazine (Compound 17, 2.0 g) obtained in Working Example 11. The solution was subjected to oxidation with a saturated aqueous solution of potassium permanganate (16 ml) to give 1-tert-butoxycarbonyl-4-[(2R,3R)-3-(2,4-difluorophenyl)-3-hydroxy-4-(1H-1,2,4-triazol-1-yl)-2butylsulfenyl]piperazine (Compound 18, 0.95 g) as colorless powder.

IR$\nu$ cm$^{-1}$ (KBR): 3420, 1695, 1615, 1500, 1420, 1360, 1245, 1165, 1135 $^1$H-NMR(CDCl$_3$) $\delta$: 1.08(3H,dd,J=7 Hz, J=2.4 Hz), 1.46(9H,s), 3.05–3.26(5H,m), 3.45–3.65(4H,m), 4.67(1H,d,J=14 Hz), 5.36(1H,d,J=14 Hz), 6.00(1H,s,OH), 6.70–6.90(2H,m), 7.40–7.55(1H,m), 7.83(1H,s), 7.93(1H,s)

Working Example 13

In dichloromethane (60 ml) was dissolved 1-tert-butoxycarbonyl-4-[(2R,3R)-3-(2,4-difluorophenyl)-3-hydroxy-4-(1H-1,2,4-triazol-1-yl)-2-butylsulfenyl]piperazine (Compound 17, 2.9 g) obtained in Working Example 11. To the solution was, added portionwise, under ice-cooling, m-Chloroperbenzoic acid (3.2.0 g), and the mixture was stirred for 2 hours at room temperatures. The reaction mixture was washed with an aqueous solution of sodium hydrogencarbonate, dried and concentrated. The concentrate was subjected to silica gel chromatography (eluent: hexane/ethyl acetate=$\frac{1}{2}$) for purification. The object fraction was concentrated to give 1-tert-butoxycarbonyl-4-[(2R,3R)-3-(2,4-difluorophenyl)-3-hydroxy-4-(1H-i, 2,4-triazol-1-yl) -2-butylsulfonyl]piperazine (Compound 19, 1.98 g) as a colorless solid substance.

m.p. 106°-110° C. IR$\nu$ cm$^{-1}$ (KBr): 3530, 1705, 1615, 1500, 1420, 1320, 1140 $^1$H-NMR (CDCl$_3$) $\delta$: 1.15(3H,d,J=7 Hz), 1 48(9H,s), 3.30–3.65(8H,m), 3.82(1H,q,J=7 Hz), 5.01(1H,d,J=14 Hz), 5.03(1H,s), 5.22(1H,d,J=14 Hz), 6.68–6.83(2H,m), 7.24–7.38(1H,m), 7.70(1H,s), 7.89(1H,s)

Working Example 14

In ethyl acetate (50 ml) was dissolved 1-tert-butoxycarbonyl-4-[(2R,3R)-3-(2,4-difluorophenyl-3-hydroxy-4-(1h-1,2,4-triazol-1-yl)-2-butylsulfonyl]piperazine (Compound 19, 1.9 g). To the solution was added a 4N-hydrochloric acid ethyl acetate solution (25 ml), and the mixture was stirred for 30 minutes at room temperatures. The reaction mixture was concentrated to dryness, and the concentrate was crystallized from methanol-ethyl acetate to give 1-[(2R,3R)-3-(2,4- difluorophenyl)-3hydroxy-4-(1H-2,4-triazol-1-yl)-2-butylsulfonyl]piperazine (Compound 20).dihydrochloride (1.72 g) as a colorless solid substance.

IR$\nu$ cm$^{-1}$ (KBr): 3430, 1610, 1500, 1420, 1330, 1300, 1140, 1130

$^1$H-NMR (DMSO-d$_6$) $\delta$: 1.08(3H,d,J=7 Hz), 3.18(4H,m), 3.63(4H,m), 4.00(1H,d,J=7 Hz), 4.88(1H,d,J=14 Hz), 5.20(1H,d,J=14 Hz), 6.70–7.00(2H,m), 7.77(1H,s), 8.57(1H,s)

Working Example 15

In dichloromethane (40 ml) was dissolved bis[(2R,3R)-3-(2,4-difluorophenyl-3-hydroxy-4-(1H-1,2,4-triazol-1-yl)-2-butyl]disulfide (1.5 g). To the solution was added dropwise, under ice-cooling, a carbon tetrachloride solution (3.3 ml) containing chlorine (0.23 g). The reaction mixture was stirred for 5 minutes under ice-cooling, to which was added 4-bromoaniline (1.34 g), followed by dropwise addition of triethylamine (0.72 ml). The reaction mixture was stirred for 15 minutes under ice-cooling, which was then washed with water, dried and concentrated. The concentrate was subjected to a silica gel chromatography (eluent: hexane/ethyl acetate=$\frac{1}{2}$) for purification to give N-(4-bromophenyl)-[(2R,3R)-3-(2,4-difluorophenyl)-3-hydroxy-4-(1H-1,2,4-triazol-1-yl)- 2butane]sulfenamide (Compound 21, 1.62 g) as a pale brown solid substance.

IR$\nu$ cm$^{-1}$ (KBr): 3380, 1610, 1590, 1500, 1480, 1270 $^1$H-NMR (CDCl$_3$) $\delta$: 1.07(3H,d,J=7 Hz), 3.34(1H,dq,J=1.4 Hz, J=7 Hz), 4.93(1H,d,J=14 Hz), 5.00(1H,s), 5.14(1H,d,J=14 Hz), 6.68–6.82(2H,m), 6.96(2H,dt,J=2 Hz, J=9 Hz), 7.33(2H,dt,J=2 Hz, J=9 Hz), 7.30–7.50(1H,m), 7.81(1H,m), 7.84(1H,s)

Working Example 16

In dichloromethane (40 ml) was dissolved N-(4-bromophenyl)-[(2R,3R)-3-(2,4-difluorophenyl)-3-hydroxy4-(1H-1, 2,4-triazol-1-yl) -2-butane]sulfenamide (Compound 21, 1.31 g) obtained in Working Example 15. To the solution was added portionwise, under ice-cooling, m-chloro perbenzoic acid (1.75 g), and the mixture was stirred for 14 hours at room temperatures. The reaction mixture was washed with an aqueous solution of sodium hydrogen carbonate, dried and concentrated. The concentrate was subjected to a silica gel chromatography (eluent: hexane/ethyl acetate=½) for purification. The object fraction was concentrated to give N-(4-bromophenyl)-[(2R, 3R)-3-(2,4-difluorophenyl)-3-hydroxy-4-(1H-1,2,4-triazol-1-yl)-2-butane]-sulfonamide (Compound 22) as a colorless solid substance. This product was processed with hydrogen chloride, followed by recrystallization from methanol-ethyl acetate, to give Compound 22.hydrochloride (868 mg) as colorless prisms.

m.p.164°–178° C. IR$\nu$ cm$^{-1}$ (KBr): 1615, 1590, 1490, 1420, 1330, 1150, 1135 $^1$H-NMR (DMSO-d$_6$) δ: 1.06 (3H, d, J=7 Hz), 3.78(1H,q,J=7 Hz), 4.82(1H,d,J=14 Hz), 5.32(1H,d,J=14 Hz), 6.87(1H,m), 7.04–7.25(2H,m), 7.27(2H,d,J=9 Hz), 7.56(2H,d,J=9 Hz), 7.75(1H,s), 8.62(1H,s)

Working Example 17

Using bis[(2R,3R)-3-(2,4-difluorophenyl-3-hydroxy-4-(1H-1,2,4-triazol-1-yl)-2-butyl]disulfide (1.5 g), chlorine (0.23 g), N-phenylpiperazine (1.05 g) and triethylamine (0.72 ml), substantially the same procedure as in Working Example 15 was allowed to proceed to give 1-[(2R,3R)-3-(2,4-difluorophenyl)-3-hydroxy-4-(1H-1,2,4-triazol-1-yl) -2,butylsulfenyl]-4-phenylpiperazine. This product was dissolved in acetone (70 ml), to which was added a saturated aqueous solution of potassium permanganate (70 ml) to cause oxidation. The reaction mixture was subjected to filtration, and the filtrate was concentrated. The concentrate was dissolved in ethyl acetate, washed with water, dried and concentrated. The concentrate was subjected to a silica gel chromatography (eluent: hexane/ethyl acetate=1/1) for purification to give 1-[(2R,3R)-3-(2,4-difluorophenyl)-3-hydroxy-4-(1H-1, 2,4-triazol-1-yl)-2-butylsulfonyl]-4-phenylpiperazine (Compound 23, 312 mg) as pale yellow powder.

m.p.135°–137° C. IR$\nu$ cm$^{-1}$ (KBr): 3430, 1615, 1600, 1500, 1340, 1280, 1130
$^1$H-NMR (CDCl$_3$)67 : 1.20(3H,d,J=7 Hz), 3.27(4H,m), 3.64 (4H,m), 3.86(1H,q,J=7 Hz), 5.03(1H,s) 5.03 (1H,dd,J=14 Hz, J=1 Hz), 5.23(1H,d,J=14 Hz), 6.68–6.85(2H,m), 6.90–7.02(3H,m), 7.28–7.40(3H,m), 7.69(1H,s), 7.90(1H,s)

Working Example 18

In dichloromethane (10 ml) was dispersed 1-[(2R,3R)-3-(2,4-difluorophenyl)-3-hydroxy-4-(1H-1,2,4-triazol-1-yl)-2-butylsulfonyl]piperazine.dihydrochloride (Compound 20, 0.20 g) obtained in Working Example 14. To the dispersion were added, under ice-cooling, triethylamine (0.20 ml) and 4-trifluoromethylbenzoyl chloride (0.13 g). The mixture was stirred for 30 minutes at room temperatures. The reaction mixture was then concentrated under reduced pressure. The concentrate was dissolved in ethyl acetate, washed with water, dried and concentrated. The concentrate was subjected to a silica gel chromatography (eluent: hexane/ethyl acetate=½) for purification. The object fraction was concentrated which was processed with hydrogen chloride, followed by adding thereto isopropylether to give 1-[(2R,3R)-3-(2,4-difluorophenyl)-3-hydroxy-4-(1H-1,2,4-triazol-1-yl)-2-butylsulfonyl]-4-(4-trifluoromethylbenzoyl)piperazine (Compound 24).hydrochloride (167 mg) as colorless powder.

IR$\nu$ cm$^{-1}$ (KBr): 3420, 1630, 1610, 1500, 1435, 1320 1120, $^1$H-NMR (DMSO-d$_6$) δ: 1.04(3H,d,J=7 Hz), 3.30–3.85(8H,m), 3.89(1H,q,J=7 Hz), 4.88(1H,d,J=14 Hz), 5.19(1H,d,J=14 Hz), 6.91(1H,m), 7.08–7.28(2H,m), 7.68(2H,d,J=8 Hz), 7.69(1H,s), 7.84(2H,d,J=8 Hz), 8.52(1H,s)

Working Example 19

In dichloromethane (10 ml) was dispersed 1[(2R,3R)-3-(2,4-difluorophenyl)-3-hydroxy-4-(1H ,1,2,4-triazol-1-yl)-2-butylsulfonyl]piperazine.dihydrochloride (Compound 20, 0.40 g) obtained in Working Example 14. To the dispersion were added, under ice-cooling, triethylamine (0.40 ml) and acetic anhydride (0.13 g). The mixture was stirred for 30 minutes under ice-cooling. The reaction mixture was then washed with water, dried and concentrated. The concentrate was subjected to a silica gel chromatography (eluent: dichloromethane/methanol=20/1) for purification. The object fraction was concentrated and processed with hydrogen chloride, followed by addition of isopropyl ether to give 1-acetyl-4-[(2R,3R)-3-(2,4-difluorophenyl)-3-hydroxy-4-(1H-1,2,4-triazol-1-yl)-2-butylsulfonyl]piperazine (Compound 25).hydrochloride (336 mg) as colorless powder.

IR$\nu$ cm$^{-1}$ (KBr): 3430, 1615, 1500, 1420, 1315, 1140 $^1$H-NMR (DMSO-d$_6$) δ: 1.04(3H,d,J=7 Hz), 2.03(3H,s), 3.20–3.60(8H,m), 3.88(1H,q,J=7 Hz), 4.89(1H,d,J=15 Hz), 5.20(1H,d,J=15 Hz), 6.90(1H,m), 7.10–7.25(2H,m), 7.78(1H,s), 8.60(1H,s)

Working Example 20

In methanol (6 ml) were dissolved 1-[(2R,3R)-3-(2,4-difluorophenyl)-3-hydroxy-4-(1H-1,2,4-triazol-1-yl)-2-butylsulfonyl]piperazine-dihydrochloride (Compound 20, 0.40 g) and 3-chloromethyl-4-methyl-4H1,2,4-triazole.hydrochloride (255 mg). To the solution was added 1N-methanol solution of sodium methylate (3.69 ml), and the mixture was heated at 70° C. for 14 hours, then the reaction mixture was concentrated. The concentrate was dissolved in dichloromethane (30 ml), washed with water, dried and concentrated. The concentrate was recrystallized from ethyl acetate to give 1-[(2R,3R)-3-(2,4-difluorophenyl)-3-hydroxy-4-(1H-1, 2,4-triazol-1-yl)-2-butylsulfonyl]-4-(4-methyl-4H-1,2,4-triazol-3-ylmethyl) piperazine (Compound 26, 108 mg) as pale yellow crystals.

m.p.210°–211° C. IR$\nu$ cm$^{-1}$ (KBr): 3430, 1615, 1530, 1500, 1320, 1270, 1140, 1120 $^1$H-NMR (CDCl$_3$) δ: 1.16(3H,d,J=7 Hz), 2.67(3H,d,J=7 Hz), 3.50(4H,m), 3.77(3H,s) , 3.82(2H,s), 5.00(1H,d,J=14 Hz), 5.03(1H,s), 5.20(1H,d,J=14 Hz), 6.68–6.84(2H,m), 7.25–7.40(1H,m), 7.69(1H,s), 7.88(1H,s), 8.12(1H,s)

Working Example 21

Using bis[(2R,3R)-3-(2,4-difluoropfenyl)-3-hydroxy-4-(1H-1,2,4-triazol-1-yl)-2-butyl]disulfide (2.0 g), chlorine (0.31 g) and pyrrolidine (1.0 g), substantially the same reaction as in Working Example 15 was allowed to proceed to give 1-[(2R,3R)-3-(2,4-difluorophenyl)-3-hydroxy-4-(1H-1,2,4-triazol-1-yl)-2-butylsulfenyl]pyrrolidine (Compound 27). This product was dissolved in acetone (70 ml), which was oxidized with a saturated aqueous solution of potassium permanganate (50 ml). The reaction mixture was subjected to filtration. The filtrate was concentrated, which was dissolved in ethyl acetate. The solution was washed with water, dried and concentrated. The concentrate was subjected to a silica gel chromatography (eluent: hexane/ethyl acetate=½) for purification to give 1-[(2R,3R)-3-(2,4-difluorophenyl)-3-hydroxy-4-(1H-1,2,4-triazol-1-yl)-2-butylsulfonyl]pyrrolidine (Compound 28, 0.58 g) as colorless needles.

m.p.149°–150° C. IR$\nu$ cm$^{-1}$ (KBr): 1610, 1500, 1320, 1185, 1320 $^1$H-NMR (CDCl$_3$) δ: 1.20(3H,d,J=7 Hz), 1.98(4H,m), 3.50(4H,m), 3.89(1H,q,J=7Hz), 4.94(1H,s), 5.04(1H,d,J=15 Hz), 5.16(1H,d,J=15 Hz), 6.67–6.84 2H,m), 7.33(1H,m), 7.65(1H,s), 7.98(1H,s)

Working Example 22

In dichloromethane (5 ml) was dispersed (RS)-1-(1-chlorosulfonylcyclopropyl)-1-(2,4-difluorophenyl)2-(1H-1,2,4-triazol-1-yl)ethyl acetate (50 mg). To the dispersion were added n-butylamine (80 mg) and 4-dimethyl aminopyridine (13.8 mg), and the mixture was stirred for 14 hours at room temperatures. To the reaction mixture was added ethyl acetate (30 ml), which was washed with water, dried and concentrated. The concentrate was subjected to a silica gel chromatography (eluent: hexane/ethyl acetate =½) for purification. The object fraction was concentrated, followed by recrystallization from isopropyl ether to give (RS)-1-(1-N-butylsulfamoylcyclopropyl)-1-(2,4-difluorophenyl)-2-(1H-1,2,4-triazol-1-yl)ethyl acetate (Compound 29, 11 mg) as colorless needles.

m.p.119°–121° C. IR$\nu$ cm$^{-1}$ (KBr): 1750, 1690, 1510 1365, 1290, 1265, 1210, 1135

$^1$H-NMR(CDCl$_3$) δ: 0.84(3H,t,J=7 Hz), 0.75–1.70.(8H,m), 2.07(1H,s), 2.55(1H,m), 2.83(2H,m), 5.52(1H,d,J=14 Hz), 6.11(1H,d,J=14 Hz), 6.84–7.10(2H,m), 7.54(1H,m), 7.97(1H, s), 8.39(1H,s)

SIMS(m/z): 443 (MH+)

Working Example 23

In dichloromethane (15 ml) was dissolved (2R 3R)-3-chlorosulfonyl-2-(2,4-difluorophenyl)-1-(1H-1,2,4-triazol-1-yl)-2-butyl acetate (0.5 g). To the solution was added, under ice-cooling, 1-phenylpiperazine (0 27 g) The reaction mixture was stirred for 10 minutes under ice-cooling, which was then concentrated. The concentrate was subjected to a silica gel chromatography (eluent: hexane/ethyl acetate=½→ethyl acetate) for purification to give, as the first eluate, 1-[3-(2,4-difluorophenyl)-4-(1H-1,2,4-triazol-1-yl)-2-buten-2-ylsulfonyl]-4-phenylpiperazine (isomer B, Compound 31, 0.05 g) as a pale brown solid substance and, as the second eluate, 1-[3-(2,4-difluorophenyl)-4-(1H-1,2,4-triazol-1-yl)-2-buten-2-ylsulfonyl]-4-phenylpiperazine (isomer A, Compound 30, 0.18 g) as a pale brown solid substance.

Isomer A

IR$\nu$ cm$^{-1}$ (neat): 1590, 1500, 1330, 1260, 1220, 1160, 1130 $^1$H-NMR(CDCl$_3$) δ: 2.34(3H,s), 3.15(4H,m), 3.32(4H,m), 4.95(1H,d,J=15 Hz), 5.24(1H,d,J=15 Hz), 6.65–7.00(6H,m), 7.20–7.35(2H,m), 7.70(1H,s), 7.89(1H,s)

Isomer B

IR$\nu$ cm$^{-1}$ (neat): 1590, 1500, 1330, 1260, 1220, 1160, 1135 $^1$H-NMR(CDCl$_3$): 1.89(3H,s), 3.30(4H,m), 3.57(4H,m), 5.49(1H,d,J=15 Hz), 5.90(1H,d,J=15 Hz), 6.75–7.10(6H,m), 7.25–7.40(2H,m), 7.79(1H,s), 7.94(1H,s)

Working Example 24

In dichloromethane (4 ml) was dissolved (2R,3R)-3-chlorosulfonyl-2-(2,4-difluorophenyl)-1-(1H-1,2,4-triazol-1-yl)-2-butyl acetate (125 mg). To the solution was added, under ice-cooling, n-butylamine (23 mg). The reaction mixture was stirred for 20 minutes under ice-cooling, which was concentrated. The concentrate was subjected to a silica gel chromatography (eluent: hexane/ethyl acetate=½→ethyl acetate) for purification to give, as the first eluate, N-butyl-3- (2,4-difluorophenyl)-4-(1H-1,2,4-triazol-1-yl) -2-butene-2-sulfonamide (isomer B, Compound 33, 10 mg) as a colorless oily substance, and, as the second eluate, N-butyl-3-(2,4-difluorophenyl)-4-(1H-1, 2,4-triazol-1-yl) -2-butene-2-sulfonamide (isomer A, Compound 32, 45 mg) as a colorless solid substance.

Isomer A m.p. 120°–121° C. IR$\nu$ cm$^{-1}$ (neat): 1610, 1590, 1500, 1420, 1330, 1270, 1160, 1140, 1120 $^1$H-NMR(CDCl$_3$) δ: 0.90(3H,t,J=7 Hz), 120–1.55(4H,m), 2.45(3H,s), 2.94(2H,m),4.14(1H,t,J=6 Hz,NH), 4.98(1H,d,J=15 Hz), 5.23(1H,d,J=15 Hz), 6.70–6.90(3H,m), 7.72(1H,s), 7.88(1H,s)

Isomer B IR$\nu$ cm$^{-1}$ (neat): 1610, 1505, 1420, 1320, 1270, 1165, 1140, 1120 $^1$H-NMR(CDCl$_3$) δ0.97(3H,t,J=7 Hz) , 1.25–1.65(4H,m), 1.93(3H,s), 3.18(2H,m), 5.45–5.80(3H,m) , 6.75–7.05(3H,m), 7.82(1H,s), 7.85(1H,s)

Working Example 25

In dichloromethane (15 ml) was dissolved (2R,3R)-3-chlorosulfonyl-2-(2,4-difluorophenyl)-1-(1H-1,2,4-triazol-1-yl)-2-butyl acetate (3.0 g). To the solution was added, under ice-cooling, dimethylamine (0.6 g). The reaction mixture was stirred for 10 minutes under ice-cooling, which was then concentrated. The concentrate was subjected to a silica gel chromatography (eluent: hexane/ethyl acetate=½→ethyl acetate) for purification to give, as the first eluate, N,N-dimethyl-3-(2,4-difluorophenyl)-4-(1H-1,2,4-triazol-1-yl)-2-butene-2-sulfonamide (isomer B, Compound 35, 0.48 g) as a pale yellow oily substance, and, as the second eluate, N,N-dimethyl-3-(2,4-difluorophenyl)-4-(1H-1,2,4-triazol-1-yl)-2-butene-2-sufonamide (isomer A, Compound 34, 0.80 g) as a pale yellow oily substance.

Isomer A

IR$\nu$ cm$^{-1}$ (neat): 1630, 1605, 1500, 1420, 1330, 1270, 1160, 1135, 1120 $^1$H-NMR(CDCl$_3$) δ: 2.40(3H,s), 2.73(6H,s), 4.95(1H,d,J=15 Hz), 5.24(1H,d,J=15 Hz), 6.65–6.85(3H,m), 7.69(1H,s), 7.89(1H,s)

Isomer B

IR$\nu$ cm$^{-1}$ (neat): 1630, 1605, 1500, 1420, 1335, 1265, 1160, 1135, 1120 $^1$H-NMR(CDCl$_3$) δ: 1.85(3H,s), 2.99(6H,s), 5.51(1H,d,J=15 Hz), 5.87(1H,d,J=15 Hz), 6.75–7.00(3H,m), 7.77(1H,s), 7.98(1H,s)

Working Example 26

A dichloromethane (30 ml) solution of (2R,3R)-3-chlorosulfonyl-2-(2,4-difluorophenyl)-1-(1H-1,2,4-triazol-1-yl)-2-butyl acetate (2.0 g) was cooled to −30° C., to which was introduced ammonia for 10 minutes. To the mixture was introduced nitrogen to eliminate ammonia. To the reaction mixture was added ethyl acetate (50 ml), then precipitating crystals were collected by filtration, followed by recrystallization from methanol to give 3-(2,4-difluorophenyl)-4-(1H-1,2,4-triazol-1-yl)-2-butene-2-sulfonamide (isomer A, Compound 36, 0.54 g) as colorless crystals.

The filtrate was subjected to distillation under reduced pressure, then the residue was subjected to a silica gel chromatography (eluent: ethyl acetate) for purification, followed by recrystallization from ethyl acetate-isopropyl ether to give 3-(2,4-difluorophenyl)-4-(1H-1,2,4-triazol-1-yl)-2-butene- 2-sulfonamide (isomer B, Compound 37, 0.60 g) as colorless crystals.

Isomer A m.p.240°-247° C. IR$\nu$ cm$^{-1}$ (KBr): 3220, 1610, 1590, 1500, 1420, 1320, 1270, 1160, 1130 $^1$H-NMR(DMSO-d6) $\delta$: 2.36(3H,s), 5.11(1H,d,J=15 Hz), 5.29(1H,d,J=15 Hz), 6.75-6.95(2H,m), 7.00-7.20(1H,m), 7.13(2H,s,NH$_2$), 7.88(1H,s), 8.19(1H,s)

Isomer B m.p.152°-153° C. IR$\nu$ cm$^{-1}$ (KBr): 3300, 1610, 1585, 1505, 1325, 1170, 1130 $^1$H-NMR(DMSO-d6) $\delta$: 1.99(3H,s), 5.57(1H,br), 5.29(1H,br), 6.09(2H,s,NH$_2$), 6.76°-6.96(3H,m), 7.81(1H,s), 7.90(1H,s)

Working Example 27

Using bis[(2R,3R)-3-(2,4-difluorophenyl)-3-hydroxy-4-(1H-1,2,4-triazol-1-yl)-2-butyl]disulfide (3.0 g), chlorine (0.47 g), 2,2,2-trifluoroethylamine hydrochloride (2.15 g) and triethylamine (4.04 ml), substantially the same reaction as in Working Example 15 was allowed to proceed to give N-(2,2,2-trifluoroethyl)-[ (2R,3R)-3-(2,4-difluorophenyl)-3-hydroxy-4-(1H-1,2,4-triazol-1-yl)-2-butane]sulfenamide (Compound 38) as a crude product. This product was dissolved in acetone (80 ml), which was oxidized with a saturated aqueous solution of potassium permanganate (30 ml). Thus oxidized product was subjected to a silica gel chromatography (eluent: hexane/ethyl acetate=$\frac{1}{2}$) for purification to give N-(2,2,2-trifluoroethyl)-[(2R,3R)-3-(2,4-difluorophenyl)-3-hydroxy-4-(1H-1,2,4-triazol-1-yl)-2-butane]sulfonamide (Compound 39, 1.91 g) as colorless powder.

IR$\nu$ cm$^{-1}$ (KBr): 1615, 1500, 1330, 1275, 1135 $^1$H-NMR(CDCl$_3$) $\delta$: 1.18(3H,d,J=7 Hz), 3.80-3.96(3H,m), 4.93(1H,dd,J=15 Hz, J=15 Hz, J=1.2 Hz), 5.43(1H,d,J=15 Hz), 5.45(1H,br), 5.63(1H,m), 6.70-6.85(2H,m), 7.20-7.35(1H,m), 7.77(1H,s), 7.79(1H,s)

Working Example 28

Using bis[(2R,3R)-3-(2,4-difluorophenyl)-3-hydroxy-4-(1H-1,2,4-triazol-1-yl)-2-butyl]disulfide (1.0 g), chlorine (0.16 g), 3 - aminomethyl - 4 -methyl - 4H-1,2,4-triazole (0.47 g) and triethylamine (0.61 ml), substantially the same reaction as in Working Example 15 was allowed to proceed to give a crude product of N-(4-methyl-4H-1,2,4-triazol-3-ylmethyl) -[(2R,3R) -3-(2,4-difluorophenyl -3-hydroxy-4-(1H-1,2,4-triazol-1-yl) -2-butane]sulfenamide (Compound 40 ). This product was dissolved in acetone (50 ml), which was oxidized with a saturated aqueous solution of potassium permanganate (8.5 ml), followed by purification by means of a silica gel chromatography (eluent: hexane/ethyl acetate=$\frac{1}{2}$) to give N-(4-methyl-4H-1,2,4-triazol-3-ylmethyl)-[(2R,3R)-3-(2,4-difluorophenyl)-3-hydroxy-4-(1H-1,2,4-triazol-1-yl)-2-butane]sulfonamide (Compound 41, 102 mg) as pale yellow powder.

IR$\nu$ cm$^{-1}$ (KBr): 1615, 1500, 1310, 1270, 1140 $^1$H-NMR(CDCl$_3$) $\delta$: 1.24(3H,d,J=7 Hz), 3.83(3H,s), 4.00(1H,q,J=7 Hz), 4.68(2H,d,J=6 Hz), 4.95(1H,d,J=15 Hz), 5.32(1H,s), 5.40(1H,d,J=15 Hz), 6.68-6.85(2H,m), 7.13(1H,t,J=6 Hz), 7.32(1H,m), 7.67(1H,s), 7.92(1H,s), 8.13(1H,s)

Working Example 29

To dichloromethane (10 ml) was added (2R,3R)-3-amino-2-(2,4-difluorophenyl)-1-(1H-1,2,4-triazol-1-yl)-2-butanol (0.54 g). To the mixture was added, under ice-cooling, triethylamine (0.28 ml), to which was added dropwise methanesulfonyl chloride (0.15 ml), followed by stirring for 15 minutes at room temperatures. To the mixture was added water (20 ml), which was subjected to extraction with dichloromethane (30 ml). The extract was washed with water (20 ml) and dried (MgSO$_4$). Then the solvent was distilled off under reduced pressure. The residue was purified by means of a silica gel chromatography (2.9×30 cm, eluent: ethyl acetate/methanol =25/1). The object fraction was concentrated to give N-[(2R,3R)-3-(2,4-difluorophenyl)-3-hydroxy-4-(1H-1,2, 4-triazol-1-yl)-2-butyl]methanesulfonamide (Compound 49, 0.52 g) as a colorless oily product. $^1$H-NMR(CDCl$_3$) $\delta$: 1.04(3H,d,J=6.6 Hz), 3.07(3H,s), 4.12-4.21(1H,m), 4.81(1H,d,J=14 Hz), 4.97(1H,d,J=14 Hz), 5.28(1H,d,J=10 Hz), 6.69-6.82(2H,m), 7.27-7.39(1H,m), 7.79(2H,s)

This product (0.5 g) was processed with 4N-hydrogen chloride-ethyl acetate in ethyl acetate to give Compound 49.hydrochloride (0.55 g) as colorless prisms. m.p. 159°-161° C. Elemental Analysis for C$_{13}$H$_{16}$F$_2$N$_4$O$_3$S.HCl: Calcd.: C, 40.78; H, 4.48; N, 14.63 Found: C, 40.60; H, 4.44; N, 14.52

Working Example 30

In substantially the same manner as in Working Example 29, (2R,3R)-3-amino-2-(2,4-difluorophenyl)-1-(1H-1,2,4-triazol-1-yl)-2-butanol (0.54 g) was allowed to react with 2,4-difluorobenzenesulfonyl chloride (0.42 g) in the presence of triethylamine (0.28 ml) to give Compound 50 (0.39 g) as a colorless oily product. $^1$H-NMR(CDCl$_3$) $\delta$: 0.73(3H,d,J=6.8 Hz), 4.05-4.13(1H,m), 4.85(1H,d,J=14 Hz), 4.97(1H,d,J=14 Hz), 5.28(1H,s), 5.47(1H,d,J=10 Hz), 6.68-6.73(2H,$^m$), 6.93-7.09(2H,m), 7.28-7.36(1H,m), 7.79(1H,s), 7.81(1H,s), 7.93-8.04(1H,m)

This product (0.38 g) was processed with 4N-hydrogen chloride-ethyl acetate to afford Compound 50.hydrochloride (0.4 g) as colorless powdery crystals, m.p.120°-122° C. Elemental Analysis for C$_{18}$H$_{16}$F$_4$N$_4$O$_3$S.HCl: Calcd.: C, 44.96; H, 3.56; N, 11.65 Found: C, 45.27; H, 3.58;, N, 11.57

Working Example 31

In substantially the same manner as in Working Example 29, (2R,3R)-3-amino-2-(2,4-difluorophenyl)-1-(1H-1,2,4-triazol-1-yl)-2-butanol (0.8 g) was allowed to react with 4-nitrobenzenesulfonyl chloride (0.74 g) in the presence of triethylamine (0.42 ml) to give Compound 51 (0.96 g) as pale yellow needles. $^1$H-NMR(CDCl$_3$) $\delta$: 0.67(3H,d,J=7 Hz), 4.06-4.21(1H,m), 4.81(1H,d,J=14 Hz), 4.96(1H,d,J=14 Hz), 5.48(1H,d,J=10 Hz), 6.68-6.82(2H,m), 7.22-7.34(1H,m), 7.82(2H,s), 8.12(2H,d,J=9 Hz), 8.40(2H,d,J=9 Hz) m.p.146°-147° C. Elemental Analysis for C$_{18}$H$_{17}$F$_2$N$_5$O$_5$S Calcd.: C, 47.68; H, 3.78; N, 15.45 Found: C, 47.56; H, 3.82; N, 15.17

Working Example 32

To a mixture of Compound 51 (0.45 g), ferric chloride (2 mg), activated charcoal (10 mg) and methanol (6 ml) was added hydrazine-hydrate (100 μl), which was heated for 10 hours under reflux. The reaction mixture was cooled, then insolubles were filtered off, followed by distilling off the solvent under reduced pressure. To the residue was added water (20ml), which was subjected to extraction with dichloromethane (30 ml). The extract solution was washed with water (20 ml), dried ($Na_2SO_4$), then the solvent was distilled off under reduced pressure. The residue was purified by means of a silica gel chromatography (2.5×30 cm, eluent: ethyl acetate/methanol=15/1). The object fraction was concentrated to afford Compound 52 (0.2 g) as a pale yellow powdery product. $^1$H-NMR(CDCl$_3$) δ: 0.67(3H,d,J=6.6 Hz), 3.05–3.40(2H,bs), 3.90–4.01(1H,m), 4.84(2H,s), 4.93(1H,d,J=10 Hz), 5.12(1H,s), 6.66–6.79(4H,m), 7.23–7.35(1H,m), 7.71(2H,d,J=8 Hz), 7.76(1H,s), 7.79(1H,s) SIMS m/z (M+H)$^+$=424

Working Example 33

In substantially the same manner as in Working Example 29, (2R,3R)-2-(2,4-difluorophenyl)-3-methylamino-1-(1H-1,2,4-triazol-1-yl)-2-butanol (0.56 g) was allowed to react with methanesulfonyl chloride (0.15 g) in the presence of triethylamine (0.28 ml) to give N-[(2R,3R)-3-(2,4-difluorophenyl)-3-hydroxy-4-(1H-1,2,4-triazol-1-yl)-2-butyl]-N-methylmethanesulfornamide (Compound 53, 0.5 g) as colorless prisms. $^1$H-NMR(CDCl$_3$) δ: 1.04(3H,d,J=7 Hz), 2.85(3H,s), 3.13(3H,s), 4.48(1H,q,J=7 Hz), 4.67 (1H,d,J=14 Hz), 5.15(1H,d,14 Hz), 5.17(1H,s), 6.69–6.79(2H,m), 7.31–7.42 (1H,m), 7.77(1H,s), 7.84(1H,s)

m.p.56°14 58° C. Elemental Analysis for $C_{14}H_{18}F_2N_4O_3S \cdot \frac{1}{2}H_2O$: Calcd.: C, 45.52; H, 5.18; N, 15.16 Found: C, 45.80; H, 4.88; N, 14.95

SIMS m/z (M+H)$^+$=361

Working Example 34

In substantially the same manner as in Working Example 29, (2R,3R)-2-(2,4-difluorophenyl)-3-methylamino-1-(1H-1,2,4-triazol-1-yl)-2-butanol (0.56 g) was allowed to react with 2,2,2-trifluoroethanesulfonyl chloride (0.22 ml) in the presence of triethylamine (0.28 ml) to give Compound 54 (0.69 g) as colorless prisms. $^1$H-NMR(CDCl$_3$) δ: 1.07(3H,d,J=7.2 Hz), 3.21(3H,s), 3.74(2H,q,J=9.2 Hz), 4.46–4.61(2H,m), 5.20(1H,d,J=14 Hz), 5.29(1H,s), 6.71–6.80(1H,m), 7.31–7.44(1H,m), 7.78(1H,s), 7.83(1H,s) m.p.148°–150° C. Elemental Analysis for $C_{15}H_{17}F_5N_4O_3S$: Calcd.: C, 42.06; H, 4.00; N, 13.08 Found: C, 42.05; H, 3.97; N, 12.95

Working Example 35

In substantially the same manner as in Working Example 29, (2R,3R)-3-amino-2-(2,4-difluorophenyl)-1(1H-1,2,4-triazol-1-yl)-2-butanol (0.42 g) was allowed to react with 2,2,2-trifluoroethanesulfonyl chloride (0.22 ml) in the presence of triethylamine (0.28 ml) to give Compound 55 (0.41 g) as a colorless oily product. $^1$H-NMR(CDCl$_3$) δ: 1.03(3H,d,J=7 Hz), 3.77–4.03(2H,m), 4.18–4.32(1H,m), 4.73(1H,d,J=14 Hz), 4.97(1H,d,J=14 Hz), 5.39(1H,d,J=10 Hz), 6.70–6.83(2H,m), 7.29–7.39(1H,m), 7.79(1H,s), 7.82(1H,s)

This product (0.4 g) was processed with 4N-hydrogen chloride-ethyl acetate in ethyl acetate to give Compound 55.hydrochloride (0.4 g) as colorless powdery crystals.

m.p.180°–182° C. Elemental Analysis for $C_{14}H_{15}F_5N_4O_3S \cdot HCl$: Calcd.: C, 37.30; H, 3.58; N, 12.43 Found: C, 37.29; H, 3.30; N, 12.19

Working Example 36

In substantially the same manner as in Working Example 29, (2R,3R)-3-amino-2-(2,4-difluorophenyl)-1-(1H-1,2,4-triazol-1-yl)-2-butanol (1.13 g) was allowed to react with 3-chloropropanesulfonyl chloride (0.54 ml) in the presence of triethylamine (0.61 ml) to give Compound 56 (1.2 g) as colorless powder. $^1$H-NMR(CDCl$_3$) δ: 1.03 (3H,d,J=6.8 Hz), 2.26–2.41(2H,m), 3.28 (2H, t, J=7 Hz), 3.72 (2H, t, J=7 Hz), 4.06–4.23(1H,m), 4.80(1H,d,J=14 Hz), 4.99(1H,d,J=14 Hz), 5.12(1H,d,J=10 Hz), 6.71–6.82(2H,m), 7.30–7.39(1H,m), 7.78(1H,s), 7.81(1H,s)

Working Example 37

A mixture of Compound 56 (0.7 g), a 28% methanol solution of sodium methylate (0.5 g) and methanol (20 ml) was heated for 90 minutes under reflux. Methanol was distilled off under reduced pressure. To the residue was added water (20 ml), which was neutralized (pH 6.5) with 1N—HCl, followed by extraction with dichloromethane (50 ml). The extract solution was washed with water (20ml), then the solvent was distilled off under reduced pressure. The residue was purified by means of a silica gel chromatography (2.9×30 cm, eluent: ethyl acetate). The object fraction was concentrated to afford Compound 57 (0.21 g) as colorless powder.

$^1$H-NMR(CDCl$_3$) δ: 1.04(3H,d,J=7 Hz), 2.31–2.53(2H,m), 3.03–3.51(3H,m), 3.81–3.92(1H,m), 4.28(1H,q,J=7 Hz), 4.66(1H,d,J=14 Hz), 5.02(1H,d,J=14 Hz), 5.08(1H,s), 6.71–6.82(2H,m), 7.31–7.43(1H,m), 7.79(1H,s), 7.84(1H,s) Elemental Analysis for $C_{15}H_{18}F_2N_4O_3S$: Calcd.: C, 48.38; H, 4.87; N, 15.04 Found: C, 48.09; H, 4.95; N, 14.98

Working Example 38

Using bis[(2R,3R)-3-(2,4-difluorophenyl)-3-hydroxy-4-(1H-1,2,4-triazol-1-yl)-2-butyl]disulfide (2.0 g), chlorine (0.31 g), 1-[4-[2-(2-butyl)-2,3-dihydro-3-oxo-4H-1,2,4-triazol-4-yl]phenyl]piperazine-dihydrochloride (2.9 g) and triethylamine (3.18 ml), substantially the same reaction as in Working Example 15 was allowed to proceed to give a crude product of 1-[4-[2-(2-butyl)-2,3-dihydro-3-oxo-4H-1,2,4-triazol-4-yl]phenyl]-4-[(2R,3R)-3-(2,4-difluorophenyl)-3-hydroxy-4-(1H-1,2,4-triazol-1-yl)-2-butanesulfenyl]piperazine. This product was dissolved in acetone (100 ml), which was oxidized by adding a saturated aqueous solution of potassium permanganate (32 ml), followed by purification by means of a silica gel chromatography (eluent: ethyl acetate). As the first fraction, 1-[4-[2-(2-butyl)-2,3-dihydro-3-oxo-4H-1,2,4-triazol-4-yl]phenyl]-4-[(2R,3R)-3-(2,4-difluorophenyl)-3-hydroxy-4-(1H-1,2,4-triazol-1-yl)-2-butanesulfonyl]-1,2,3,4-tetrahydropyrazine (Compound 43, 37 mg) was obtained as a pale yellow solid substance. As the second fraction, 1-[4-[2-(2-butyl)-2,3-dihydro-3-oxo-4H-1,2,4-triazol-4-yl]phenyl]-4-[(2R,3R)-3-(2,4-difluorophenyl)-3-hydroxy-4-(1H-1,2,4-triazol-1-yl)-2-butane sulfonyl]piperazine (Compound 42, 743 mg) was obtained as colorless powder.

Compound 42 m.p.142°–144° C. IRν cm$^{-1}$ (KBr): 1705, 1610, 1520, 1315, 1270, 1140, 1115 $^1$H-NMR (CDCl$_3$) δ: 0.90(3H,t,J=7.4 Hz), 1.20(3H,d,J=7 Hz), 1.39(3H,d,J=6.8 Hz), 1.60–1.95(2H,m), 3.29(4H,m), 3.65(4H,m), 3.86(1H,q,J=7 Hz), 4.29(1H,m), 4.99(1H,d,J=15 Hz), 5.02(1H,s), 5.24(1H,d,J=15 Hz), 6.68–6.84(2H,m), 7.00(2H,d,J=9 Hz), 7.32(1H,m), 7.45(2H,d,J=9 Hz), 7.62(1H,s), 7.71(1H,s), 7.90(1H,s)

Compound 43 m.p.87°–95° C. IRν cm$^{-1}$ (KBr): 1700, 1610, 1520, 1335, 1270, 1150 $^1$H-NMR(CDCl$_3$) δ: 0.91(3H,t,J=7.4 Hz), 1.22(3H,d,J=7 Hz), 1.39(3H,d,J=6.8 Hz), 1.60–1.98(2H,m), 3.65–4.02(4H,m), 3.93(1H,q,J=7 Hz), 5.05(1H,d,J=15 Hz), 5.08(1H,s), 5.29(1H,d,J=15 Hz), 6.03(1H,d,J=6.6 Hz), 6.08(1H,d,J=6.6 Hz), 6.67–6.85(2H,m), 6.96(1H,d,J=9 Hz), 7.32(1H,m), 7.46(2H,d,J=9 Hz), 7.63(1H,s), 7.71(1H,s), 7.90(1H,s)

Working Example 39

Using bis[(2R,3R)-3-(2,4-difluorophenyl)-3-hydroxy-4-(1H-1,2,4-triazol-1-yl)-2-butyl]disulfide (1.62 g), chlorine (0.26 g), 1-[4-[2-(2,2,2-trifluoroethyl)-2,3-dihydro-3-oxo-4H-1,2,4-triazol-4-yl]phenyl]piperazine (2.4 g) and triethylamine (2.57 ml), substantially the same reaction as in Working Example 15 was allowed to proceed to give a crude product 1-[4-[2-(2,2,2-trifluoroethyl)-2,3-dihydro-3-oxo-4H-1,2,4-triazol-4-yl]phenyl]-4-[(2R,3R)-3-(2,4-difluorophenyl)-3-hydroxy-4-(1H-1,2,4-triazol-1-yl)-2-butanesulfenyl]piperazine. This product was dissolved in acetone (50 ml), which was oxidized with a saturated aqueous solution of potassium permanganate (3.5 ml), followed by purification by means of a silica gel chromatography (eluent: hexane/ethyl acetate=½) to afford 1-[4-[2-(2,2,2-trifluoroethyl)-2,3-dihydro-3-oxo-4H-1,2,4-triazol-4-yl]phenyl]-4-[(2R,3R)-3-(2,4-difluorophenyl)-3-hydroxy-4-(1H-1,2,4-triazol-1-yl)-2-butanesulfonyl]piperazine (Compound 44, 241 mg) as colorless powder.

m.p.237°–239° C. IRν cm$^{-1}$ (KBr): 1710, 1610, 1520, 1320, 1270, 1145 $^1$H-NMR(CDCl$_3$) δ: 1.20(3H,d,J=7 Hz), 3.03(4H,m), 3.65(4H,m), 3.87(1H,q,J=7 Hz), 4.46(2H,g,J=8.4 Hz), 5.04(1H,d,J=15 Hz), 5.08(1H,s), 5.24(1H,d,J=15 Hz), 6.67–6.85(2H,m), 7.01(2H,d,J=9 Hz), 7.32(1H,m), 7.43(2H,d,J=9 Hz), 7.71(1H,s), 7.91(1H,s)

Working Example 40

1-[(2R,3R)-3-(2,4-difluorophenyl)-3-hydroxy-4-(1H-1,2,4-triazol-1-yl)-2-butanesulfonyl]piperazine.dihydrochloride (Compound 20, 0.40 g) obtained in Working Example 14 and 2-chloropyrimidine (0.49 g) were dissolved in methanol (10 ml). To the solution was added a 1N—NaOMe methanol solution (3.36, ml), and the mixture was stirred for 24 hours at room temperatures. The reaction mixture was concentrated, to which was added ethyl acetate, followed by washing with water, drying and concentration under reduced pressure. To the concentrate was added ether to cause precipitation of crystals, followed by recrystallization from ethyl acetate-ether to afford 1-[(2R,3R)-3-(2,4-difluorophenyl)-3-hydroxy-4-(1H-1,2,4-triazol-1-yl)-2-butanesulfonyl]-4-(2-pyrimidinyl) piperazine (Compound 45., 130 mg) as colorless powder.

m.p.101°–108° C. IRν cm$^{-1}$ (KBr): 1610, 1580, 1500, 1360, 1320, 1265, 1140 $^1$H-NMR(CDCl$_3$) δ: 1.17(3H,d,J=7 Hz), 3.53(4H,m), 3.85(1H,q,J=7 Hz), 3.96(4H,m), 5.02(1H,s), 5.03(1H,dd,J=15 Hz,J=1.6 Hz), 5.23(1H,d,J=15 Hz), 6.56(1H,t,J=4.8 Hz), 6.68–6.82(2H,m), 7.31(1H,m), 7.69(1H,s), 7.90(1H,s), 8.33(2H,d,J=4.8 Hz)

Working Example 41

In methanol (15 ml) were dissolved N-(2,2,2-trifluoroethyl)-[(2R,3R)-3-(2,4-difluorophenyl)-3-hydroxy-4-(1H-1,2,4-triazol-1-yl)-2-butane]sulfonamide obtained in Working Example 27 (Compound 39, 0.50 g), methyl p-toluenesulfonate (0.50 g) and a 1N—NaOMe methanol solution (1.81 ml). The solution was stirred for 18 hours at 60° C. The reaction mixture was concentrated, to which was added ethyl acetate. The mixture was washed with water, then dried and concentrated, followed by purification by means of a silica gel chromatography (eluent: dichloromethane/ethyl acetate=10/1). The object fraction was concentrated, which was recrystallized from ether-isopropylether to afford N-methyl-N-(2,2,2-trifluoroethyl)-[(2R,3R)-3-(2,4-difluorophenyl)-3-hydroxy-4-(1H-1,2,4-triazol-1-yl)-2-butane]sulfonamide (Compound 46, 0.31 g) as colorless prisms.

m.p.122°–123° C. IRν cm$^{-1}$ (KBr): 1615, 1500, 1335, 1270, 1150, 1120 $^1$H-NMR(CDCl$_3$) δ: 1.20(3H,d,J=7 Hz), 3.16(3H,s), 3.62(1H,m), 3.91(1H,q,J=7 Hz), 4.27(1H,m), 4.97(1H,s), 5.05(1H,dd,J=15 Hz,J=1.4 Hz), 5.16(1H,d,J=15 Hz), 6.68–6.84(2H,m), 7.32(1H,m), 7.68(1H,s) 7.90(1H,s)

Working Example 42

Using bis [(2R,3R)-3-(2,4-difluorophenyl)-3-hydroxy-4-(1H-1, 2,4-triazol-1-yl)-2-butyl]disulfide (3.0 g), chlorine (0. 47 g), N-methylbenzylamine (2.56 g), substantially the same reaction as in Working Example 15 was allowed to proceed to afford N-benzyl-N-methyl-[(2R,3R)-3-(2,4-difluorophenyl)-3-hydroxy-4-(1H-1,2,4-triazol-1-yl)-2-butane]sulfonamide (Compound 47, 1.07 g) as colorless needles.

m.p.141°–143° C. IRν cm$^{-1}$ (KBr): 1610, 1500, 1325, 1270, 1150, 1140 $^1$H-NMR(CDCl$_3$) δ1.19(3H,d,J=7 Hz), 2.89(3H,s), 3.91(1H,q,J=7 Hz), 4.34(1H,d,J=14.5 Hz), 4.59(1H,d,J=14.5 Hz), 4.97(1H,s), 5.08(1H,dd,J=15 Hz,J=1.4 Hz), 5.21(1H,d,J=15 Hz), 6.68–6.86(2H,m), 7.23–7.52(6H,m), 7.67(1H,s), 7.98(1H,s)

Working Example 43

In methanol (13 ml) were dissolved N-methyl-[(2R,3R)-3-(2,4-difluorophenyl)-3-hydroxy-4-(1H-1,2,4-triazol-1-yl)-2-butane]sulfonamide (Compound 12, 0.33 g) obtained in Working Example 8, ethyl p-toluenesulfonate (0.29 g) and a 1N—NaOMe methanol solution (1.43 ml). The solution was stirred for 13 hours at 70° C. The reaction mixture was concentrated, to which was added ethyl acetate. The mixture was washed with water, dried and concentrated, followed by purification by means of a silica gel chromatography (eluent: hexane/ethyl acetate=½). The object fraction was concentrated and recrystallized form ether to give N-ethyl-N-methyl[(2R,3R)-3-(2,4-difluorophenyl)-3-hydroxy-4-(1H-1,2,4-triazol-1-yl)-2-butane]sulfonamide (Compound 48, 0.13 g) as colorless prisms.

m.p.160°–162° C. IRν cm$^{-1}$ (KBr): 1610, 1500, 1320, 1270, 1140, 1120 $^1$H-NMR(CDCl$_3$) δ: 1.15(3H,d,J=7 Hz), 1.26(3H,t,J=7.3 Hz), 2.98(3H,s), 3.20–3.55(2H,m), 3.84(1H,q,J=7 Hz), 4.89(1H,s), 5.04(1H,d,J=15 Hz), 5.14(1H,d,J=15 Hz), 6.68–6.85(2H,m), 7.33(1H,m), 7.65(1H,s), 7.99(1H,s)

Working Example 44

Using bis[(2R,3R)-3-(2,4-difluorophenyl)-3-hydroxy-4-(1H-1,2,4-triazol-1-yl)-2-butyl]disulfide (2.0 g), chlorine (0.31 g) and benzylamine (1.49 g), substantially the same reaction with Working Example 15 was allowed to proceed to afford N-benzyl-[(2R,3R)-3-(2,4-difluorophenyl)-3-hydroxy-4-(1H-1,2,4-triazol-1-yl)-2-butane]sulfonamide (Compound 58, 0.95 g) as colorless powder.

m.p.149°-150° C. IR$\nu$ cm$^{-1}$ (KBr): 1615, 1500, 1320, 1270, 1200, 1135 $^1$H-NMR(CDCl$_3$) $\delta$: 1.20(3H,d,J=7 Hz), 3.77(1H,q,J=7 Hz), 4.45(2H,m), 4.95(1H,d,J=14 Hz), 5.09(1H,t,J=5.8 Hz), 5.35(1H,d,J=14 Hz), 6.68–6.85(2H,m), 7.20–7.55(6H,m), 7.70(1H,s), 7.84(1H,s)

Working Example 45

Using bis[(2R,3R)-3-(2,4-difluorophenyl)-3-hydroxy-4-(1H-1,2,4-triazol-1-yl)-2-butyl]disulfide (1.6 g), chlorine (0.25 g) and aminodiphenylmethane (2.56 g), substantially the same reaction as in Working Example 15 was allowed to proceed to afford N-diphenylmethyl-[(2R,3R)-3-(2,4-difluorophenyl)-3-hydroxy-4-(1H-1,2,4-triazol-1-yl)-2-butane]sulfonamide (Compound 59, 0.45 g) as a colorless oily product. $^1$H-NMR(CDCl$_3$) $\delta$: 0.98(3H,d,J=7 Hz), 3.50(1H,q,J=7 Hz), 4.83(1H,dd,J=15 Hz,J=1.2 Hz), 5.18(1H,s), 5.25(1H,d,J=15 Hz), 5.85(1H,s), 6.60–6.78(2H,m), 7.15–7.60(11H,s), 7.60(1H,s), 7.80(1H,s)

This product was processed with hydrogen chloride, to which was added ether, whereupon Compound 59.hydrochloride as pale yellow powder.

m.p.120°-128° C. IR$\nu$ cm$^{-1}$ (KBr): 1610, 1500, 1420, 1310, 1145

Working. Example 46

Using bis[(2R,3R)-3-(2,4-difluorophenyl)-3-hydroxy-4-(1H-1,2,4-triazol-1-yl)-2-butyl]disulfide (2.0 g), chlorine (0.31 g) and veratrylamine (2.35 g), substantially the same reaction as in Working Example 15 was allowed to proceed to give N-(3,4-dimethoxybenzyl)-[(2R,3R)-3-(2,4-difluorophenyl)-3-hydroxy-4-(1H-1,2,4-triazol-1-yl)-2-butane]sulfonamide (Compound 60, 0.95 g) as a colorless oily product. $^1$H-NMR(CDCl$_3$) $\delta$: 1.21(3H,d,J=7 Hz), 3.78(1H,q,J=7 Hz), 3.89(3H,s), 3.90(3H,s), 4.38(2H,m), 4.93(1H,s), 4.98(1H,d,J=15 Hz), 5.32(1H,br), 5.36(1H,d,J=15 Hz), 6.70–6.95(5H,m), 7.30(1H,m), 7.72(1H,s), 7.88(1H,s)

This product was processed with hydrogen chloride, followed by addition of ether to give Compound 60.hydrochloride as colorless powder.

m.p.134°-157° C. IR$\nu$ cm$^{-1}$ (KBr): 1615, 1598, 1505, 1420, 1325, 1270, 1160, 1140

Working Example 47

Using bis[(2R,3R)-3-(2,4-difluorophenyl)-3-hydroxy-4-(1H-1,2,4-triazol-1-yl)-2-butyl]disulfide (1.0 g), chlorine (0.15 g) and N-methyldodecylamine (1.40 g), substantially the same reaction as in Working Example 15 was allowed to proceed to afford N-dodecyl-N-methyl-[(2R,3R)-3-(2,4-difluorophenyl)-3-hydroxy-4-(1H-1,2,4-triazol-1-yl)-2-butane]sulfonamide (Compound 61, 0.30 g) as a pale yellow oily product. $^1$H-NMR(CDCl$_3$) $\delta$: 0.88(3H,t,J=6.4 Hz), 1.14(3H,d,J=7 Hz), 1.27(18H,m), 1.62(2H,m), 2.97(3H,s), 3.06–3.44(2H,m), 3.85(1H,q,J=7 Hz), 4.89(1H,s), 5.03(1H,d,J=15 Hz), 5.13(1H,d,J=15 Hz), 6.68–6.84(2H,m), 7.33(1H,m), 7.63(1H,s), 7.98(1H,s)

This product was processed with hydrogen chloride, followed by addition of hexane to give Compound 61.hydrochloride as a colorless solid product.

IR$\nu$ cm$^{-1}$ (KBr): 2930, 1610, 1500, 1320, 1140

Working Example 48

In methanol (8 ml) were dissolved N-methyl [(2R,3R)-3-(2,4-difluorophenyl)-3-hydroxy-4-(1H-1,2,4-triazol-1-yl)-2-butane]sulfonamide (Compound 12, 0.40 g) obtained in Working Example 8, propargyl bromide (1.0 g) and 1N—NaOMe (6.9 ml), and the solution was stirred for 24 hours at room temperatures. To the reaction mixture was added ethyl acetate (100 ml), which was washed with water, dried and concentrated. The concentrate was purified by means of a silica gel chromatography (eluent: hexane/ethyl acetate=1/2). The object fraction was concentrated, followed by recrystallization from ethyl acetate-isopropyl ether to give N-methyl-N-(2-propinyl)-[(2R,3R)-3-(2,4-difluorophenyl)-3-hydroxy-4-(1H-1,2,4-triazol-1-yl)-2-butane]sulfonamide (Compound 62, 0.29 g) as colorless prisms.

m.p.143°-145° C. IR$\nu$ cm$^{-1}$ (KBr): 2105, 1615, 1595, 1500, 1320, 1240 $^1$H-NMR(CDCl$_3$) $\delta$: 1.22(3H,d,J=7 Hz), 2.40(1H,t,J=2.4 Hz), 3.09(3H,s), 3.92(1H,q,J=7 Hz), 4.01(1H,dd,J=18.4 Hz,J=2.4 Hz), 4.33(1H,dd,J=18.2 Hz,J=2.4 Hz), 4.92(1H,s), 5.03(1H,dd,J=15 Hz,J=1.6 Hz), 5.19(1H,d,J=15 Hz), 6.68–6.86(2H,m), 7.33(1H,m), 7.67(1H,s), 7.94(1H,s)

Working Example 49

In methanol (10 ml) were dissolved N-methyl-[(2R,3R)-3-(2,4-difluorophenyl)-3-hydroxy-4-(1H-1,2,4-triazol-1-yl)-2-butane]sulfonamide (Compound 12, 0.51 g) obtained in Working Example 8, 4,4-dimethyl-2-pentynyl p-toluene sulfonate (1.77 g) and 1N—NaOMe methanol solution (5.3 ml). The solution was stirred for 13 hours at room temperatures. The reaction mixture was concentrated under reduced pressure, to which was added ethyl acetate (50 ml), followed by washing with water, drying and concentration. The concentrate was subjected to a silica gel chromatography (eluent: hexane/ethyl acetate=1/1) for purification. The object fraction was concentrated to give N-(4,4-dimethyl-2-pentynyl)-N-methyl-[(2R,3R)-3-(2,4-difluorophenyl)-3-hydroxy-4-(1H-1,2,4-triazol-1-yl)-2-butane]sulfonamide (Compound 63, 0.46 g) as a pale yellow solid product.

IR$\nu$ cm$^{-1}$ (KBr): 2980, 2230, 1610, 1500, 1330, 1135 $^1$H-NMR(CDCl$_3$) $\delta$: 1.18(9H,s), 1.21(3H,d,J=7 Hz), 3.06(3H,s), 3.92(1H,d,J=18 Hz), 3.96(1H,g,J=7 Hz), 4.35(1H,d,18 Hz), 4.80(1H,s), 5.05(1H,dd,J=15 Hz,J=1.6 Hz), 5.17(1H,d,J=15 Hz), 6.68–6.82(2H,m), 7.33(1H,m), 7.65(1H,s), 7.98(1H,s)

Working Example 50

Using bis[(2R,3R)-3-(2,4-difluorophenyl)-3-hydroxy-4-(1H-1,2,4-triazol-1-yl)-2-butyl]disulfide (3.0 g), chlorine (0.47 g) and 3-(N-methylaminomethyl)pyridine (2.6 g), substantially the same reaction as in Working Example 15 was allowed to proceed to give N-(3-pyridylmethyl)-N-methyl-[(2R,3R)-3-(2,4-difluorophenyl)-3-hydroxy-4-(1H-1,2,4-triazol-1-yl)-2-butane]sulfonamide Compound 64, 1.1 g) as an oily product. $^1$H-NMR(CDCl$_3$) $\delta$: 1.22(3H,d,J=7 Hz), 2.89(3H,s), 3.93 (1H,q,J=7 Hz), 4.38(1H,d,J=15 Hz), 4.60(1H,d,J=15 Hz), 5.06(1H,dd,J=14.6 Hz,J=1.6 Hz), 5.07(1H,s), 5.23(1H,d,J=14.6 Hz), 6.70–6.86(2H,m), 7.27–7.41(2H,m), 7.69(1H,s), 7.82(1H,m), 7.92(1H,s), 8.59(2H,m)

This product was processed with hydrogen chloride to give hydrochloride as colorless glass.

IR$\nu$ cm$^{-1}$ (KBr): 3350, 1616, 1558, 1500, 1423, 1326, 1132 Elemental Analysis for C$_{19}$H$_{21}$F$_2$N$_5$O$_3$S.2HCl.H$_2$O Calcd.: C, 43.18; H, 4.77; N, 13.25 Found: C, 43.24; H, 4.92; N, 12.99

Working Example 51

In toluene (200 ml) were dissolved N-(3,4-dimethoxybenzyl)-[(2R,3R)-3-(2,4-difluorophenyl)-3-hydroxy-4-(1H-1,2,4-triazol-1-yl)-2-butane]sulfonamide (Compound 60, 0.71 g) obtained in Working Example 46, ethanol (0.75 g) and sulfuric acid (0.63 g), and the solution was stirred for 30 minutes at 70° C. After cooling, saturated sodium bicarbonate was added to the reaction mixture for neutralization, and then the solvent was dissolved off under reduced pressure. To the residue were added ethyl acetate and water to separate into two layers. The organic layer was washed with water, then dried, which was concentrated under reduced pressure. The concentrate was purified by means of a silica gel column chromatography (eluent: hexane/ethyl acetate=½). The object fraction was concentrated, followed by recrystallization from methanol-dichloromethan to give (2R,3R)-3-(2,4-difluorophenyl)-3-hydroxy-4-(1H-1,2,4-triazol-1-yl)-2-butanesulfonamide (Compound 65, 0.34 g) as colorless prisms.

m.p.195°–197° C. IR$\nu$ cm$^{-1}$ (KBr): 3410, 1610, 1500, 1315, 1275, 1165 $^1$H-NMR(CDCl$_3$) $\delta$: 1.24(3H,d,J=7 Hz), 3.84(1H,q,J=7 Hz), 4.92(1H,d,J=7 Hz), 4.93(2H,br-s), 5,53 (1H,d,J=15 Hz), 5.77(1H,d,J=1.4 Hz), 6.70–6.84(2H,m), 7.27(1H,m), 7.77(1H,s), 7.78(1H,s)

SIMS: 333 (MH$^+$)

Working Example52 using bis[(2R,3R)-3-(2,4-difluorophenyl)-3-hydroxy-4-(1H-1,2,4-triazol-1-yl)-2-butyl]disulfide (2.0 g), chlorine (0.25 g) and N-methyl-4-trifluoromethylbenzylamine (2.64 g), substantially the same reaction as in Working Example 15 was allowed to proceed to give N-methyl-N-(4-trifluoromethylbenzyl)-[(2R,3R)-3-(2,4-difluorophenyl)-3-hydroxy-4-(1H-1,2,4-triazol-1-yl)-2-butane]sulfonamide (Compound 66, 0.21 g) as white powder.

IR$\nu$ cm$^{-1}$ (KBr): 1620, 1500, 1325, 1124 $^1$H-NMR(CDCl$_3$) $\delta$: 1.23(3H,d,J=7 Hz), 2.90(3H,s), 3.92(1H,q,J=7 Hz), 4.41(1H,d,J=15 Hz), 4.65(1H,d,J=15 Hz), 5.04(1H,s), 5.07(1H,d,J=14 Hz), 5.23(1H,d,J=14 Hz), 6.70–6.90(2H,m), 7.25–7.45(1H,m), 7.52(2H,d,J=8.4 Hz), 7.67(2H,d,J=8.4 Hz), 7.70(1H,s), 7.94(1H,s)

Working Example 53

Using bis[(2R,3R)-3-(2,4-difluorophenyl)-3-hydroxy-4-(1H-1,2,4-triazol-1-yl)-2-butyl]disulfide (1.0 g), chlorine (0.i3 g) and N-methyl-2-fluoro-4-trifluoromethylbenzylamine (1.3 g), substantially the same reaction as in Working Example 15 was allowed to proceed to give N-(2-fluoro-4-trifluoromethylbenzyl)-N-methyl-[(2R,3R)-3-(2,4-difluorophenyl)-3-hydroxy-4-(1H-1,2,4-triazol-1-yl)-2-butane]sulfonamide (Compound 67, 0.19 g) as white powder.

IR$\nu$ cm$^{-1}$ (KBr): 1620, 1500, 1430, 1331, 1128 $^1$H-NMR(CDCl$_3$) $\delta$: 1.21(3H,d,J=7 Hz), 2.96(3H,s), 3.89(1H,q,J=7 Hz), 4.46(1H,d,J=15.5 Hz), 4.72(1H,d,J=15.5 Hz), 5.02(1H,br), 5.06(1H,dd,J=14.6 Hz,J=1.6 Hz), 5.21(1H,d,J=14.6 Hz), 6.68–6.85(2H,m), 7.05–7.70(4H,m), 7.71(1H,s), 7.99(1H,s)

Working Example 54

In methanol (10 ml) were dissolved N-methyl-[(2R,3R)-3-(2,4-difluorophenyl)-3-hydroxy-4-(1H-1,2,4-triazol-1-yl)-2-butane]sulfonamide (Compound 12, 0.30 g) obtained in Working Example 8, 6,6-dimethyl-2-hepten-4-enylbromide (0.40 g) and 1N—NaOMe (2 ml), and the solution was stirred for 14 hours at room temperature. Ethyl acetate (100 ml) was added to the reaction mixture which was then washed with water, dried and concentrated. Thereafter, the resultant mixture was subjected to a silica gel column chromatography (eluent: hexane/ethyl acetate=1/1) for purification. Further, an isomer was separated by reverse phased chromatography using ODS column, thereby obtaining N-[(E)-6,6-dimethyl-2-hepten-4-ynyl]-N-methyl-[(2R,3R)-3-(2,4-difluorophenyl)-3-hydroxy-4-(1H-1,2,4-triazol-1-yl)-2-butane]sulfonamide (Compound 68, 110 mg) as a first eluate and N-[(Z)-6,6-dimethyl-2-hepten-4-ynyl]-N-methyl (2R,3R)-3-(2,4-difluorophenyl)-3-hydroxy-4-(1H-1,2,4-triazol-1-yl)-2-butane]sulfonamide (Compound 69, 60 mg) as a second eluate.

Compound 68

IR$\nu$ cm$^{-1}$ (KBr): 1618, 1500, 1327, 1140 $^1$H-NMR(CDCl$_3$) $\delta$: 1.16(3H,d,J=7 Hz), 1.25(9H,s), 2.94(3H,s), 3.81(1H,dd,J=15.6 Hz,J=6.5 Hz), 3.84(1H,q,J=7 Hz), 4.01(1H,dd,J=15.6 Hz,J=6.5 Hz), 4.95(1H,s), 5.03(1H,d,J=14.6 Hz), 5.16(1H,d,J=14.6 Hz), 5.72(1H,d,J=15.8 Hz), 5.97(1H,dt,J=15.8 Hz,J=6.4 Hz), 6.68–6.85(2H,m), 7.33(1H,m), 7.66(1H,s), 7.95(1H,s)

Compound 69

IR$\nu$ cm$^{-1}$ (KBr): 1620, 1500, 1324, 1272, 1140 $^1$H-NMR(CDCl$_3$) $\delta$: 1.18(3H,d,J=7 Hz), 1.27(9H,s), 2.97(1H,s), 3.87(1H,q,J=7 Hz), 4.03(1H,dd,J=14.6 Hz,J=6 Hz), 4.22(1H,dd,J=14.6 Hz,J=6 Hz), 4.94(1H,s), 5.05(1H,d,J=15 Hz), 5.17(1H,d,J=15 Hz), 5.76(1H,d,J=10.6 Hz), 5.86(1H,dt,J=10.6 Hz,J=6.4 Hz), 6.68–6.85(2H,m), 7.34(1H,m), 7.65(1H,s), 7.97(1H,s)

Working Examples 55–59

Compounds 70, 71, 72, 73 and 74were obtained by the same manner as in Working Example 44.

Working Example 55

4-[(2R,3R)-3-(2,4-difluorophenyl)-3-hydroxy-4-(1H-1,2,4-triazol-1-yl)-2-butanesulfonyl]-1-[4-(2,2,2-trifluoroethoxy)phenyl]piperazine (Compound 70)

IR$\nu$ cm$^{-1}$ (KBr): 3446, 1618, 1511, 1321, 1145 $^1$H-NMR(CDCl$_3$) $\delta$: 1.20(3H,t,J=7 Hz), 3.16(4H,m), 3.62(4H,m), 3.85(1H,q,J=7 Hz), 4-31(2H,q,J=8 Hz), 5.03(1H,dd,J=14.6 Hz,J=14.6 Hz), 5.03(1H,s), 5.22(1H,d,J=14.6 Hz), 6.68–6.85(2H,m), 6.91(4H,s), 7.69(1H,s), 7.91(1H,s)

Working Example 56

4-[(2R,3R)-3-(2,4-difluorophenyl)-3-hydroxy-4-(1H-1,2,4-triazol-1-yl)-2-butanesulfonyl]-1(4-fluorophenyl)piperazine (Compound 71)

m.p.128°–130° C. IR$\nu$ cm$^{-1}$ (KBr): 3400, 1620, 1510, 1325, 1150 $^1$H-NMR(CDCl$_3$) $\delta$: 1.20(3H,t,J=7 Hz), 3.17(4H,m), 3.63(4H,m), 3.85(1H,q,J=7 Hz), 5.03(1H,dd,J=14.6 Hz,J=1.4 Hz), 5.03(1H,s), 5.22(1H,d,J=14.6 Hz), 6.68–7.10(6H,m), 7.32(1H,m), 7.69(1H,s), 7.90(1H,s)

Working Example 57

4-[(2R,3R)-3-(2,4-difluorophenyl)-3-hydroxy-4-(1H-1,2,4-triazol-1-yl)-2-butanesulfonyl]-1-(4-methoxyphenyl)piperazine (Compound 72)

m.p. 190°–191° C. IR$\nu$ cm$^{-1}$(KBr): 3500, 1620, 1515, 1500, 1320, 1150 $^1$H-NMR(CDCl$_3$) δ: 1.20(3H,t,J=7 Hz), 3.13 (4H,t,J=5 Hz), 3.63(4H,m), 3.78(3H,s), 3.85(1H,q,J=7 Hz), 5.01(1H,s), 5.04(1H,d,J=14.6 Hz), 5.22(1H,d,J=14.6 Hz), 6.67–6.95(2H,m), 7.33(1H,m), 7.68(1H,s), 7.91(1H,s)

Working Example 58

4-[(2R,3R)-3-(2,4-difluorophenyl)-3-hydroxy-4-(1H-1,2,4-triazol-1-yl)-2-butanesulfonyl]-1-(4-trifluoromethylphenyl)piperazine (Compound 73)

m.p. 158°–159 ° C. IR$\nu$ cm$^{-1}$(KBr): 1620, 1500, 1330, 1150, 1120 $^1$H-NMR(CDCl$_3$) δ: 1.20(3H,d,J=7 Hz), 3.36(4H,m), 3.63(4H,m), 3.86(1H,q,J=7 Hz), 5.03(1H,d,J=14.4 Hz), 5.08(1H,s), 5.25(1H,d,J=14.4 Hz), 6.70–6.85(2H,m), 6.95(2H,d,J=8.6 Hz), 7.25–7.40(1H,m), 7.53(2H,d,J=8.6 Hz), 7.71(1H,s), 7.89(1H,s)

Working Example 59

4-[(2R,3R)-3-(2,4-difluorophenyl)-3-hydroxy-4-(1H-1,2,4-triazol-1-yl)-2-butanesulfonyl]-1-(2-pyridyl)piperazine (Compound 74)

IR$\nu$ cm$^{-1}$ (KBr): 1595, 1500, 1440, 1310, 1140 $^1$H-NMR(CDCl$_3$) δ: 1.18(3H,d,J=7 Hz), 3.54–3.75(8H,m), 3.85(1H,q,J=7 Hz), 5.04(1H,dd,J=14.6 Hz,J=1.4 Hz), 5.03(1H,s), 5.23(1H,d,J=14.6 Hz), 6.65–6.83(4H,m), 7.32(1H,m), 7.54(1H,m), 7.70(1H,s), 7.91(1H,s), 8.21(1H,m)

Working Example 60

In methanol (10 ml) were dissolved N-methyl-[(2R,3R)-3-(2,4-difluorophenyl)-3-hydroxy-4-(1H-1,2,4-triazol-1-yl)-2-butane]sulfonamide (Compound 12, 0.55 g) obtained in Working Example 8, N-methyl-2-chloromethylimidazole.hydrochloride (1.20 g) and 1N—NaOMe (14.4 ml), and the solution was stirred for 4 hours at 60° C. After cooling, ethyl acetate (100 ml) was added to the reaction mixture which was then washed with water, dried and concentrated. Thereafter, the resultant mixture was subjected to a silica gel column chromatography (eluent: ethyl acetate/methanol =10/1) for purification, thereby obtaining Compound 75 (0.12 g) as an oily product. $^1$H-NMR(CDCl$_3$) δ: 1.22(3H,d,J=7 Hz), 2.99(3H,s), 3,73(3H,s), 3.98(1H,q,J=7 Hz), 5.01(1H,dd,J=14.6 Hz,J=1.4 Hz), 5.19(1H,d,J=14.6 Hz), 6,50(1H,br), 6,70–6.85(2H,m), 6.90(1H,s), 6.98(1H,s), 7.36(1H,m), 7.63(1H,s), 7.99(1H,s)

This product was processed with hydrogen chloride, followed by recrystallization from ethyl acetate to give Compound 75.dihydrochloride (0.13 g) as colorless powder.

IR$\nu$ cm$^{-1}$ (KBr): 3400, 1618, 1500, 1330, 1150, 1130

Working Example 61

Compound 76 was prepared by the same manner as in Working Example 60.

Compound 76 m.p. 140°–142 ° C. IR$\nu$ cm$^{-1}$(KBr): 1595, 1500, 1360, 1340, 1320, 1145 $^1$H-NMR(CDCl$_3$) δ: 1.23(3H,d,J=7 Hz), 2.92(3H,s), 3.94(1H,g,J=7 Hz), 4.36(1H,d,J=15.6 Hz), 4.61(1H,d,J=15.6 Hz), 5.06(1H,d,J=14.6 Hz), 5.09(1H,s), 5.23(1H,d,J=14.6 Hz), 6.70–6.85(2H,m), 7.28–7.40(1H,m), 7.32(2H,d,J=5 Hz), 7.69(1H,s), 7.92(1H,s), 8.63(2H,d,J=5 Hz)

Working Example 62

Using bis[(2R,3R)-3-(2,4-difluorophenyl)-3-hydroxy-4-(1H-1,2,4-triazol-1-yl)-2-butyl]disulfide (2.0 g), chlorine (0.25 g) and 2-methylaminopyrimidine (1.54 g), substantially the same reaction as in Working Example 15 was allowed to proceed to give N-methyl-N-(2-pyrimidinyl)-[(2R,3R)-3-(2,4-difluorophenyl)-3-hydroxy-4-(1H-1,2,4-triazol-1-yl)-2-butane]sulfonamide (Compound 77, 0.11 g) as a colorless prism.

m.p. 150°–151 ° C. IR$\nu$ cm$^{-1}$(KBr): 1616, 1564, 1508, 1442, 1396, 1349, 1199 hu 1H-NMR(CDCl$_3$) δ: 1.21(3H,d,J=7 Hz), 3.59(3H,s), 5.08(1H,s), 5.15(1H,q,J=7 Hz), 5.19(1H,dd,J=15 Hz,J=6 Hz), 5.32(1H,d,J=15 Hz), 6.70–6.83(2H,m), 7.06(1H,t,J=4.8 Hz), 7.38(1H,m), 7.68(1H,s), 7.97(1H,s), 8.63(1H,d,J=4.8 Hz)

Working Examples 63–68

Compounds 78, 79, 80, 81, 82 and 83 were prepared by the same manner as in Working Example 62.

Working Examples 63

Compound 78 m.p. 121°–123 ° C. IR$\nu$ cm$^{-1}$(KBr): 1616, 1500, 1328, 1139 $^1$H-NMR(CDCl$_3$ ) δ: 1.20(3H,d,J=7 Hz), 3.06(3H,s), 4.00(1H,q,J=7 Hz), 4.07(1H,d,$^J$=16 Hz), 4.95(1H,d,$^J$=16 Hz), 5.04(1H,d,J=14.6 Hz), 5.24(1H,s), 5-24(1H,d,$^J$=14.6 Hz), 6.70–6.86(2H,m), 7.34(1H,m), 7.41(1H,d,$^J$=3-4 Hz), 7.67(1H,s), 7.78(1H,d,$^J$=3.4 Hz), 7.93(1H,s)

Working Example 64

Compound 79

IR$\nu$ cm$^-$(KBr): 1612, 1500, 1340, 1130 $^1$H-NMR(CDCl$_3$) δ: 1.23(3H,d,J=7 Hz), 2.90(3H,s), 3.93(1H,q,J=7 Hz), 4.40(1H,d,J=15 Hz), 4.65(1H,d,J=15 Hz), 5.03(1H,s), 5.05(1H,d,$^J$=14.6 Hz), 5.23(1H,d,J=14.6 Hz), 6.65–6.85(4H,m), 7.32(1H,m), 7.56(1H,m), 7.70(1H,s), 7.92(1H,s), 8.20(1H,m)

Working Example 65

Compound 80

IR$\nu$ cm$^{-1}$ (KBr): 1620, 1500, 1420, 1330, 1140 $^1$H-NMR(CDCl$_3$) δ: 1.12(3H,d,$^J$=7 Hz), 2.45(3H,s), 3.01(3H,s), 3-13(2H,t,J=7.5 Hz), 3.30–3.68(2H,m), 3.82(1H,q,J=7 Hz), 4.91(1H,s), 5.03(1H,d,$^J$=14.6 Hz), 5.14(1H,d,J=14.6 Hz), 6.65–6.82(2H,m), 7.25–7.38(1H,m), 7.66(1H,s), 7.93(1H,s), 8.62(1H,s)

Working Example 66

Compound 81

IR$\nu$ cm$^{-1}$ (KBr): 3420, 1618, 1520, 1407, 1370, 1272, 1120 $^1$H-NMR(CDCl$_3$) δ: 1.24(3H,d,J=7 Hz), 2.52(3H,s), 3.77(3H,s), 3.89(1H,q,J=7 Hz), 5.07(1H,dd,J=14.6 Hz), 5.17(1H,s), 5.29(1H,d,J=14.6 Hz), 6.65–6.84(2H,m), 7.33(1H,m), 7.62(1H,s), 8.01(1H,s) SIMS: 445(MH+)

Working Example 67

Compound 82

IR$\nu$ cm$^{-1}$ 1615, 1500, 1330, 1128 $^1$H-NMR(CDCl$_3$) δ: 1.23(3H,d,J=7 Hz), 2.80(3H,s), 3.03(3H,s), 3-93(1H,q,J=7 Hz), 4.73(1H,d,J=16 Hz), 4.95(1H,d,J=16 Hz), 5.11(1H,d,J=14.6 Hz), 5.16(1H,s), 5.25(1H,d,J=14.6 Hz), 6.80–6.86(2H,m), 7.25–7.42(1H,m), 7.71(1H,s), 7.87(1H,s)

Working Example 68

Compound 83

IR$\nu$ cm$^{-1}$ (KBr): 1614, 1500, 1390, 1325, 1144 $^1$H-NMR(CDCl$_3$) δ: 1.16(3H,d,J=7 Hz), 2.77(3H,s), 3.05(3H,s), 3.40(2H,t,J=7 Hz), 3.84 (1H, q,J=7 Hz), 3,60–3.90(2H,m), 4.92(1H,s), 5.03(1H,d,J=14.6 Hz), 5.14(1H,d,J=14.6 Hz), 6.68–6.83(2H,m), 7.25–7.38(1H,m), 7.66(1H,s), 7.92(1H,s)

Working Example 69

In dichloromethane was dissolved N-methyl-N-[2-(5-methylthio-1,3,4-thiadiazol-2-yl]-[(2R,3R)-3-(2,4-difluorophenyl)-3-hydroxy-4-(1H-1,2,4-triazol-1-yl)-2-butane]sulfonamide (Compound 83, 0.30 g) obtained in Working Example 68 and then oxidized with m-chloroperbenzoate (0.30 g). The reaction mixture was washed with bicarbonate solution, dried and concentrated. The residue was purified by means of a silica gel chromatography to give Compound 84 (0.20 g) as colorless powder.

IR$\nu$ cm$^{-1}$ (KBr): 1618, 1500, 1330, 1160 $^1$H-NMR(CDCl$_3$) δ: 1.16(3H,d,J=7 Hz), 3.08(3H,s), 3.47(3H,s), 3.57(2H,t,J=6.7 Hz), 3.68–4.13(2H,m), 3.87(1H,d,J=7 Hz), 4.99(1H,d,J=15 Hz), 5.01(1H,s), 5.20(1H,d,J=15 Hz), 6.78–6.86(2H,m), 7.15–7.39(1H,m), 7.69(1H,s), 7.91(1H,s)

Working Example 70

Using bis[(2R,3R)-3-(2,4-difluorophenyl)-3-hydroxy-4-(1-imidazolyl)-2-butyl]disulfide (0.5 g), chlorine (0.13 g) and 20% dimethylamine-toluene solution (1.6 g), substantially the same reaction as in Working Example 1 was allowed to proceed to give N,N-dimethyl-[(2R,3R)-3-(2,4-difluorophenyl)-3-hydroxy-4-(1-imidazolyl)-2-butane]sulfonamide (Compound 85, 109 mg) as white powder.

IR$\nu$ cm$^{-1}$ (KBr): 1620, 1450, 1330, 1150 $^1$H-NMR(CDCl$_3$) δ: 1.12(3H,d,J=7 Hz), 3.02(6H,s), 3.94(1H,q,J=7 Hz), 4.60(1H,br,OH), 4.77(2H,s), 6.71(1H,s), 6.70–6.86(2H,m), 6.75(1H,s), 7.25(1H,s), 7.39(1H,m) SIMS=360 (MH+)

Working Example 71

Using bis[(2R,3R)-3-(2,4-difluorophenyl)-3-hydroxy-4-(1-imidazolyl)-2-butyl]disulfide (0.5 g), chlorine (0.23 g) and N-methyl-4-trifluoromethylbenzylamine (0.85 g), substantially the same reaction as in Working Example 15 was allowed to proceed to give N-methyl-N-(4-trifluoromethylbenzyl)-[(2R,3R)-3-(2,4-difluorophenyl)-3-hydroxy-4-(1-imidazolyl)-2-butane]sulfonamide (Compound 86, 110 mg) as a colorless oily product. This product was processed with hydrochloric acid, followed by recrystallization from methanol-ether to give hydrochloride (82 mg).

IR$\nu$ cm$^{-1}$ (KBr): 1620, 1500, 1327, 1125 $^1$H-NMR(CDCl$_3$) δ: 1.17(3H,d,J=7 Hz), 2.90(3H,s), 3.97(1H,q,J=7 Hz), 4.37(1H,d,J=15 Hz), 4.54(1H,br), 4.63(1H,d,J=15 Hz), 4.80(1H,s), 6.70–6.83(2H,m), 6.72(1H,s), 6.76(1H,s), 7.26(1H,s), 7.40(1H,m), 7.50(2H,d,J=8 Hz), 7.67(2H,d,J=8 Hz)

Working Example 72

(2R,3R)-3-Amino-2-(2,4-difluorophenyl)-1-(1H-1,2,4-triazol-1-yl)-2-butanol (0.54 g) was added to dichloromethane (10 ml), to which triethylamine (0.28 ml) was added under ice-cooling. Thereafter, 2-thiophene sulfonylchloride (0.42 g) was dropwise added to the resultant mixture, followed by stirring for 15 hours at room temperature. To the resultant mixture was added water (20 ml) for extraction with dichloromethane (30 ml). The extract solution was washed with water and dried (MgSO$_4$), then the solvent was distilled off under reduced pressure. The residue was purified by means of a silica gel chromatography (silica gel: 60 g, eluent: dichloromethane/ethyl acetate=½). The object fraction was concentrated to afford Compound 87 (0.45 g) as an colorless oily product. $^1$H-NMR(CDCl$_3$) δ: 0.72(3H,d,J=7 Hz), 4.10(1H,q,J=7 Hz), 4.76–4.95(2H,m), 5.24(1H,s), 5.27(1H,d,J=14 Hz), 6.69–6.80(2H,m), 7.09–7.69(4H,m), 7.76(1H,s), 7.80(1H,s)

This product (0.45 g) was processed with 4N-hydrogen chloride-ethyl acetate in ethyl acetate to give Compound 87.hydrochloride (0.46 g) as colorless powder.

m.p. 138°–140 °C. Elementary Analysis for C$_{16}$H$_{16}$F$_2$N$_4$O$_3$S$_2$·HCl·½H$_2$O Calcd.: C, 41.78; H, 3.94; N, 12.18 Found: C, 41.92; H, 3.92; N, 12.23

Working Examples 73–75

Using (2R,3R)-2-(2,4-difluorophenyl)-3-methylamino-1-(1H-1,2,4-triazole-1-yl)-2-butanol, substantially the same reaction as in Working Example 72 was allowed to proceed to give Compounds 88, 89 and 90.

Working Example 73

Compound 88 $^1$H-NMR(CDCl$_3$) δ: 1.13(3H,d,J=7 Hz), 3.24(3H,s), 3.97(3H,s), 4.63–4.79(2H,m), 5.23(1H,d,J=14 Hz), 5.24(1H,s), 6.67–6.82(2H,m), 6.97(1H,s), 7.06(1H,s), 7.32–7.44(1H,m), 7.78(1H,s), 7.85(1H,s) m.p. 95–96° C. Elementary Analysis for C$_{17}$H$_{20}$F$_2$N$_6$O$_3$S Calcd.: C, 47.88; H, 4.73; N, 19.71 Found: C, 47.63; H, 4.67; N, 19.46

Working Example 74

Compound 89

1H-NMR(CDCl$_3$) δ: 0.81(3H,d,J=7 Hz), 2.28(3H,s), 2.60(3H,s), 3.12(3H,s), 4.57(1H,d,J=14 Hz), 4.75(1H,d,J=14 Hz), 5.17(1H,s), 5.21(1H,d,J=14 Hz), 6.70–6.84(2H,m), 7.35–7.41(1H,m), 7.79(1H,s), 7.86(1H,s), 9.48(1H,s) SIMS: m/z(M+H)+ =501

Working Example 75

Compound 90 $^1$H-NMR(CDCl$_3$) δ: 0.63(3H,d,J=7 Hz), 3.09(3H,s), 4.55(1H,q,J=7 Hz), 4.77(1H,d,J=14 Hz), 5.17(1H,s), 5.21(1H,d,J=14 Hz), 6.71–6.82(2H,m), 7.11–8.20(4H,m), 7.79(1H,s), 7.85(1H,s)

This product was isolated as hydrochloride.

m.p. 127°–129° C. Elementary Analysis for C$_{17}$H$_{18}$F$_2$N$_4$O$_3$S$_2$·HCl Calcd.: C, 43.92; H, 4.12; N, 12.05 Found: C, 43.92; H, 4.38; N, 12.03

Working Example 76

In methanol (6 ml) was dissolved 1-[(2R,3R)-3-(2,4-difluorophenyl)-3-hydroxy-4-(1H-1,2,4-triazol-1-yl)-2-butanesulfonyl]piperazine.dihydrochloride (Compound 20, 0.40 g) and 2,4-dichloro-5-fluoropyrimidine (0.32 g). The solution was stirred for 6 hours at 60 °C. The reaction mixture was concentrated, and the residue was purified by means of a silica gel chromatography (eluent: hexane/ethyl acetate=½) to give Compound 91 (0.18 g) as white powder. $^1$H-NMR(CDCl$_3$) δ: 1.17(3H,d,J=7 Hz), 3.61(4H,m), 3.85(1H,q,J=7 Hz), 3.93(4H,m), 5.01(1H,d,J=14.6 Hz), 5.26(1H,s), 5.26(1H,d,J=14.6 Hz), 6.70–6.84(2H,m), 7.23–7.36(1H,m), 7.72(1H,s), 7.84(1H,s), 8.00(1H,d,J=6 Hz)

Working Example 77

In ethanol (30 ml) was dissolved 1-[(2R,3R)-3-(2,4-difluorophenyl)-3-hydroxy-4-(1H-1,2,4-triazol-1-yl)-2-butanesulfonyl]-4-(2-chloro-5-fluoropyrimidin-4-yl)piperazine (Compound 91, 120 mg), sodium acetate and 10% palladium carbon (60 mg). The solution was stirred for 5 hours at 40 °C. in the atmosphere of hydrogen. The catalyst was filtered off, and the filtrate was concentrated. The residue was extracted with ethyl acetate to distill off the solvent. The residue was purified by means of a silica gel chromatography to give Compound 92 (71 mg) as white powder.

IRν cm$^{-1}$ (KBr): 3080, 1620, 1605, 1500, 1330, 1140
$^1$H-NMR(CDCl$_3$) δ: 1.17(3H,d,J=7 Hz), 3.61(4H,m), 3.86(1H,q,J=7 Hz), 3.91(4H,m), 5.02(1H,d,J=14.6 Hz), 5.14(1H,s), 5.26(1H,d,J=14.6 Hz), 6.70–6.84(2H,m), 7.31(1H,m), 7.72(1H,s), 7.88(1H,s), 8.16(1H,d,J=6 Hz), 8.45(1H,d,J=3 Hz)

Working Example 78

In methanol (10 ml) were dissolved N-methyl-[(2R,3R)-3-(2,4-difluorophenyl)-3-hydroxy-4-(1H-1,2,4-triazol-1-yl)-2-butane]sulfonamide (Compound 12, 0.40 g), 3-chloromethylpyridine.hydrochloride (853 mg) and 1N—NaOMe (10.4 ml). The solution was stirred for 4 hours at 60 °C. The reaction mixture was concentrated, and the residue was extracted with ethyl acetate. The extract was washed with water and dried. The solvent was distilled off under reduced pressure, and the residue was purified by means of a silica gel chromatography (eluent: ethyl acetate/methanol=10/1) to give Compound 64 (0.18 g) as colorless oily product. 1H-NMR of this product was the same as that of Compound 64 obtained in Working Example 60.

Working Example 79

To dimethylformamide (30 ml) were added (2R,3R)-2-(2,4-difluorophenyl)-1-(1H-1,2,4-triazol-1-yl)-3-methanesulfonylamino-2-butanol.hydrochloride (2.14 g) and 3-chloromethylpyridine hydrochloride (0.92 g). 60% Oily sodium hydride (0.45 g) was added portionwise to the reaction mixture, while stirring under ice-cooling. The reaction mixture was stirred for 15 hours at room temperature, poured into ice-water (100 ml) and extracted with ethyl acetate (100 ml×2). The extract was washed with saturated saline solution and dried. The solvent was distilled off under reduced pressure, and the residue was purified by means of a silica gel chromatography (silica gel: 50 g, eluent: ethyl acetate/methanol=30/1 →10/1). The object fractions were concentrated to crystallize from isopropylether to give Compound 93 (0.25 g) as white powder.

m.p. 204°–206° C. $^1$H-NMR(CDCl$_3$) δ: 1.21(3H,d,J=7 Hz), 2.71(3H,s), 4.43–4.69(3H,m), 4.87(2H,d,J=14 Hz), 5.12(1H,s), 5.16(1H,d,J=14 Hz), 6.69–6,79(2H,m), 7.29–7.40(2H,m), 7.72(1H,s), 7.77(1H,s), 8.02(1H,m), 8.57(1H,m), 8.78(1H,m)

Working Example 80

Compound 94 was prepared by the same manner as in Working Example 79.

m.p. 88°–90° C. $^1$H-NMR(CDCl$_3$) δ: 1.17(3H,d,J=7 Hz), 2.80(3H,m), 4.50–4.66(3H,m), 4-79(1H,d,J=14 Hz), 5.04(1H,s), 5.15(1H,d,J=14 Hz), 6.69–6.81(2H,m), 7.24–7.36(1H,m), 7.50(2H,d,J=6 Hz), 7.71(1H,s), 7.76(1H,s), 8.63(2H,d,J=6 Hz)

Working Example 81

Compound 95 was prepared by the same manner as in Working Example 79.

1H-NMR(CDCl$_3$) δ: 1.19(3H,d,J=7 Hz), 2.70(3H,s), 4.51–4.68(3H,m), 4.90(1H,d,$^J$=14 Hz), 5.07(1H,s), 5.18(1H,d,J=14 Hz), 6.70–6.85(2H,m), 7.30–7.42(1H,m), 7.60–7.77(6H,m)

Preparation 1

The components (1), (2), (3) and (4) stated below were mixed. The mixture was packed in gelatin capsules to obtain capsules, each of which contains the Compound 2 in an amount of 50 mg.

| | |
|---|---|
| (1) Compound 2 (obtained in Working Example 1) | 50 mg |
| (2) Lactose | 100 mg |
| (3) Cornstarch | 40 mg |
| (4) Magnesium stearate | 10 mg |
| Total | 200 mg |

Preparation 2

The Compound 49 and magnesium stearate were granulated in a solution of soluble starch. The resultant product was dried, and then mixed with lactose and cornstarch. The mixture was subjected to compression molding to obtain a tablet containing the components (1), (2), (3), (4) and (5) stated below.

| | |
|---|---|
| (1) Compound 49 (obtained in Working Example 29) | 50 mg |
| (2) Lactose | 65 mg |
| (3) Cornstarch | 30 mg |
| (4) Soluble starch | 35 mg |
| (5) Magnesium stearate | 20 mg |
| Total | 200 mg |

What we claim is:

1. An azole compound represented by the formula (I):

$$\underset{N}{\overset{X}{\underset{\diagup}{\diagdown}}}N-CH_2-\underset{Ar}{\overset{R^7}{\underset{|}{C}}}-\underset{R^2}{\overset{R^1}{\underset{|}{C}}}-\overset{(O)_n}{\overset{\parallel}{S}}-N\underset{R^4}{\overset{R^3}{\diagdown}} \quad (I)$$

wherein X is a nitrogen atom;

Ar is a phenyl group substituted by halogen or a halogenated $C_{1-4}$ alkyl group;

$R^1$ and $R^2$ independently are a hydrogen atom or a lower alkyl group, or $R^1$ and $R^2$ may combine together to form a lower alkylene group;

$R^3$ and $R^4$ independently are (a) a hydrogen atom, (b) a $C_{1-12}$ alkyl group which may be substituted by (1) a hydroxyl group, (2) an optionally esterified carboxyl group selected from carboxyl, methoxycarbonyl, ethoxycarbonyl and butoxycarbonyl, (3) a nitro group, (4) an amino group, (5) a $C_{1-6}$ alkanoylamino group, (6) a $C_{1-6}$ alkylamino group, (7) a $C_{1-6}$ alkoxy group, (8) a halogen, (9) a halogenated $C_{1-3}$ alkyl group, (10) an oxo group, (11) a thioxo group, (12) a mercapto group, (13) a $C_{1-6}$ alkylthio group, (14) a $C_{1-6}$ alkylsulfonyl group, (15) a $C_{1-6}$ alkanoyl group, (16) a $C_{6-14}$ aryl group optionally substituted with (A) an optionally halogenated $C_{1-3}$ alkyl group, (B) a halogen, (C) an optionally halogenated $C_{1-3}$ alkoxy group, or (D) a 5- or 6-membered heterocyclic group containing at least one hetero atom selected from nitrogen, sulfur and oxygen, which may optionally be substituted with (i) an optionally halogenated $C_{1-6}$ alkyl group, (ii) a $C_6$ alkylsulfonyl group or (iii) a $C_{1-6}$ alkylthio group, (17) a benzoyl group optionally substituted by halogen or halogenated $C_{1-3}$ alkyl group, (18) a heterocyclic alkyl group selected from triazolylmethyl, methyltriazolylmethyl, pyridylmethyl, imidazolylmethyl and methylimidazolylmethyl, or (19) a $C_{3-6}$ cycloalkyl-alkyl group selected from cyclopropylmethyl and cyclopentylmethyl;

(c) a $C_{3-8}$ cycloalkyl group which may be substituted by the substituents as defined in (b);

(d) a $C_{2-4}$ alkenyl group which may be substituted by the substituents as defined in (b);

(e) a $C_{2-9}$ alkynyl group which may be substituted by the substituents as defined in (b);

(f) a $C_{6-14}$ aryl group which may be substituted by the substituents as defined in (b);

(g) a 5- or 6-membered heterocyclic group containing one to three hetero atoms selected from nitrogen, sulfur and oxygen, the 5- or 6-membered heterocyclic group being selected from imidazolyl, triazolyl, tetrazolyl, pyrazolyl, pyridyl, thiazolyl, thiadiazolyl, thienyl, furyl, pyrrolyl, pyrazinyl, 4-piperidinyl, 1-piperazinyl, pyrimidinyl, isoxazolyl, oxazolyl, N-methylimidazolyl and N-methyltriazolyl, which may be substituted by the substituents as defined in (b); or (h) $R^3$ and $R^4$ may form a non-aromatic 5- or 6-membered heterocyclic group together with the nitrogen atom to which they are bonded further containing at least one hetero atom selected from nitrogen, sulfur and oxygen, the non-aromatic 5- or 6-membered heterocyclic group being selected from morpholino, piperidino, 1-piperazinyl, 1-pyrrolidinyl, 1,2,3,4-tetrahydropyrazin-1-yl, 1-indolinyl, 2-isoindolinyl, 1,2,3,4-tetrahydroquinolin-1-yl, 1,2,3,4-tetrahydroisoquinolin-2-yl, imidazoly, triazolyl, tetrazolyl, pyrrolyl and pyrazolyl, which may be substituted by the substituents as defined in (b);

n denotes an integer of 0 to 2; and $R^7$ is a hydrogen atom, a hydroxyl group which may be optionally acylated by an acyl group selected from acetyl, propionyl, butyryl, isobutyryl, phenylacetyl and benzoyl, or may form a bond together with $R^1$; or a salt thereof.

2. The azole compound of claim 1 or a salt thereof in which $R^1$ is a hydrogen atom, $R^2$ is methyl group and Ar is a halogen-substituted phenyl group.

3. The azole compound of claim 1 or a salt thereof in which $R^3$ and $R^4$ independently are a hydrogen atom or a $C_{1-2}$ alkyl group which may be substituted by (1) a hydroxyl group, (2) an optionally esterified carboxyl group selected from carboxyl, methoxycarbonyl, ethoxycarbonyl and butoxycarbonyl, (3) a nitro group, (4) an amino group, (5) a $C_{1-6}$ alkanoylamino group, (6) a $C_{1-6}$ alkylamino group, (7) a $C_{1-6}$ alkoxy group, (8) a halogen, (9) a halogenated $C_{1-3}$ alkyl group, (10) an oxo group, (11) a thioxo group, (12) mercapto group, (13) a $C_{1-6}$ alkylthio group, (14) a $C_{1-6}$ alkylsulfonyl group, (15) a $C_{1-6}$ alkanoyl group, (16) a $C_{6-14}$ aryl group optionally substituted with (A) an optionally halogenated $C_{1-3}$ alkyl group, (B) a halogen, (C) an optionally halogenated $C_{1-3}$ alkoxy group, or (D) a 5- or 6-membered heterocyclic group containing at least one hetero atom selected from nitrogen, sulfur and oxygen, which may optionally be substituted with (i) an optionally halogenated $C_{1-6}$ alkyl group, (ii) a $C_{1-6}$ alkylsulfonyl group or (iii) a $C_{1-6}$ alkylthio group, (17) a benzoyl group optionally substituted by halogen or halogenated $C_{1-3}$ alkyl group, (18) a heterocyclic alkyl group selected from tirazolylmethyl, methyltriazolylmethyl, pyridylmethyl, imidazolylmethyl and methylimidazolylmethyl or (19) a $C_{3-6}$ cycloalkyl-alkyl group selected from cyclopropylmethyl and cyclopentylmethyl.

4. The azole compound of claim 1 or a salt thereof in which n is 2.

5. The azole compound of claim 2 or a salt thereof in which the carbon atom to which Ar and $R_7$ are bonded and the carbon atom to which $R^1$ and $R^2$ are bonded are R-configuration respectively.

6. The azole compound of claim 1 or a salt thereof in which $R^7$ is a hydroxyl group which may be acylated by an acyl group selected from acetyl, propionyl, butyryl, isobutyryl, phenylacetyl and benzoyl.

7. The azole compound of claim 1 which is selected from the group consisting of N, N-dimethyl- [(2R,3R) -3-(2,4-difluorophenyl)-3-hydroxy-4-(1H-1,2,4-triazol-1-yl)-2-butane]sulfonamide, N-methyl-[(2R,3R)-3-(2,4-difuorophenyl)-3-hydroxy-4- (1H-1,2,4-triazol-1-yl)-2-butane ]sulfonamide and N-(3 -pyridylmethyl)-N-methyl-[(2R,3R)-3-(2,4 -difluorophenyl)-3 -hydroxy-4 -(1H-1,2,4-triazol-1-yl) -2-butane ]sulfonamide.

8. An antifungal composition which comprises an effective amount of an azole compound represented by the formula (I) as defined in claim 1 or a salt thereof and a pharmaceutically acceptable carrier, excipient or diluent therefor.

* * * * *

UNITED STATES PATENT AND TRADEMARK OFFICE
CERTIFICATE OF CORRECTION

PATENT NO. : 5,389,663
DATED : February 14, 1995
INVENTOR(S) : Katsumi ITOH et al.

It is certified that error appears in the above-indentified patent and that said Letters Patent is hereby corrected as shown below:

In Column 61, line 11, Claim 1, contains a typographical error wherein "alkylysulfonyl" should read --alkylsulfonyl--.

Column 61, line 20, Claim 1, "(ii) a $C_6$" should read --(ii) a $C_{1-6}$--.

Column 62, line 12, Claim 3, "$C_{1-2}$" should read --$C_{1-12}$--.

Signed and Sealed this

Twenty-seventh Day of February, 1996

*Attest:*

BRUCE LEHMAN

*Attesting Officer*  *Commissioner of Patents and Trademarks*